US009844324B2

(12) United States Patent
Merritt et al.

(10) Patent No.: US 9,844,324 B2
(45) Date of Patent: Dec. 19, 2017

(54) IMAGE GUIDED NAVIGATION SYSTEM

(71) Applicant: X-Nav Technologies, LLC, Lansdale, PA (US)

(72) Inventors: Scott A. Merritt, Green Lane, PA (US); Robert W. Emery, III, McLean, VA (US); Edward J. Marandola, Gwynedd, PA (US); Christopher W. Scharff, Collegeville, PA (US)

(73) Assignee: X-Nav Technologies, LLC, Lansdale, PA (US)

( * ) Notice: Subject to any disclaimer, the term of this patent is extended or adjusted under 35 U.S.C. 154(b) by 728 days.

(21) Appl. No.: 14/209,500

(22) Filed: Mar. 13, 2014

(65) Prior Publication Data

US 2014/0272773 A1 Sep. 18, 2014

Related U.S. Application Data

(60) Provisional application No. 61/782,255, filed on Mar. 14, 2013.

(51) Int. Cl.
*A61C 19/04* (2006.01)
*A61B 5/00* (2006.01)
(Continued)

(52) U.S. Cl.
CPC ........ *A61B 5/0088* (2013.01); *A61B 1/00147* (2013.01); *A61B 1/24* (2013.01);
(Continued)

(58) Field of Classification Search
CPC ..... A61B 5/0088; A61B 1/00147; A61B 1/24; A61B 5/0077; A61B 6/032; A61B 6/12;
(Continued)

(56) References Cited

U.S. PATENT DOCUMENTS 3,878,610 A 4/1975 Coscina
5,026,278 A * 6/1991 Oxman ................ A61C 9/0006
433/37

(Continued)

FOREIGN PATENT DOCUMENTS

EP 0501993 B1 11/1997
EP 1527417 B1 5/2005
(Continued)

OTHER PUBLICATIONS

Supplementary European Search Report dated Oct. 17, 2016 (EP Appl. No. 14770737.6).

(Continued)

*Primary Examiner* — Heidi M Eide
(74) *Attorney, Agent, or Firm* — Drinker Biddle & Reath LLP

(57) ABSTRACT

An image guidance system for tracking a surgical instrument within the oral cavity. The image guidance system includes a plurality of cameras adapted to be located within the oral cavity to provide intraoral images of optically visible patterns within oral cavity. A processing system receives and processes the intraoral images to recognize patterns and triangulate the locations and orientations of each camera. The processing system uses a reference dataset which defines a reference coordinate system based on alignment to a portion of the oral anatomy. The processing system determines the location and orientation of the tracked instrument based on the reference dataset. In an embodiment, the system includes an oral fixture that is removably attachable to teeth in a patient and is configured to hold one of the cameras.

18 Claims, 17 Drawing Sheets

(51) Int. Cl.

| | | |
|---|---|---|
| *A61B 6/03* | (2006.01) | |
| *A61B 6/14* | (2006.01) | |
| *A61B 6/12* | (2006.01) | |
| *A61B 6/00* | (2006.01) | |
| *A61B 1/00* | (2006.01) | |
| *A61B 1/24* | (2006.01) | |
| *A61C 9/00* | (2006.01) | |
| *A61C 1/08* | (2006.01) | |
| *A61B 90/00* | (2016.01) | |
| *A61B 90/16* | (2016.01) | |

(52) U.S. Cl.
CPC ............ *A61B 5/0077* (2013.01); *A61B 6/032* (2013.01); *A61B 6/12* (2013.01); *A61B 6/14* (2013.01); *A61B 6/145* (2013.01); *A61B 6/4417* (2013.01); *A61B 6/5247* (2013.01); *A61C 1/082* (2013.01); *A61C 9/004* (2013.01); *A61C 19/04* (2013.01); *A61B 90/16* (2016.02); *A61B 2090/3983* (2016.02)

(58) Field of Classification Search
CPC ......... A61B 6/14; A61B 6/145; A61B 6/4417; A61B 6/5247; A61B 2090/3983; A61C 1/082; A61C 9/004; A61C 19/04; A61C 1/084; A61C 1/085
See application file for complete search history.

(56) References Cited

U.S. PATENT DOCUMENTS

| | | | |
|---|---|---|---|
| 5,588,430 A | 12/1996 | Bova et al. | |
| 5,772,432 A | 6/1998 | Jordan et al. | |
| 5,823,958 A | 10/1998 | Truppe | |
| 6,018,592 A | 1/2000 | Shinagawa et al. | |
| 6,072,903 A | 6/2000 | Maki et al. | |
| 6,096,048 A | 8/2000 | Howard, III et al. | |
| 6,223,067 B1 | 4/2001 | Vilsmeier et al. | |
| 6,368,285 B1 | 4/2002 | Osadchy et al. | |
| 6,402,707 B1* | 6/2002 | Ernst .................... | A61B 5/1076 433/214 |
| 6,611,141 B1 | 8/2003 | Schulz et al. | |
| 6,640,128 B2 | 10/2003 | Vilsmeier et al. | |
| 6,978,167 B2 | 12/2005 | Dekel et al. | |
| 7,457,443 B2* | 11/2008 | Persky .................. | A61B 6/14 128/922 |
| 7,762,814 B2 | 7/2010 | van der Zel | |
| 7,889,905 B2 | 2/2011 | Higgins et al. | |
| 7,894,878 B2 | 2/2011 | Noujeim | |
| 8,064,669 B2 | 11/2011 | Higgins et al. | |
| 8,172,573 B2 | 5/2012 | Sonenfeld et al. | |
| 8,218,905 B2 | 7/2012 | Dekel et al. | |
| 8,376,738 B2 | 2/2013 | Wagner | |
| 8,938,282 B2 | 1/2015 | Daon | |
| 2003/0156681 A1 | 8/2003 | Cianciosi et al. | |
| 2005/0034733 A1* | 2/2005 | Liddle .................. | A61F 5/566 128/859 |
| 2005/0085714 A1 | 4/2005 | Foley et al. | |
| 2006/0083422 A1 | 4/2006 | Ernst et al. | |
| 2006/0257817 A1 | 11/2006 | Shelton | |
| 2007/0106152 A1 | 5/2007 | Kantrowitz et al. | |
| 2007/0173790 A1 | 7/2007 | Moctezuma De La Barrera et al. | |
| 2008/0019579 A1 | 1/2008 | Crucs | |
| 2008/0039717 A1 | 2/2008 | Frigg et al. | |
| 2008/0138755 A1* | 6/2008 | Jansheski ............. | A61F 5/566 433/6 |
| 2008/0171305 A1* | 7/2008 | Sonenfeld ............ | A61C 1/084 433/215 |
| 2009/0209852 A1 | 8/2009 | Mate et al. | |
| 2010/0075273 A1 | 3/2010 | Karlsson et al. | |
| 2010/0142674 A1* | 6/2010 | Lee ...................... | G03B 42/042 378/54 |
| 2010/0233647 A1 | 9/2010 | Yang | |
| 2010/0286568 A1 | 11/2010 | Xia et al. | |
| 2011/0008751 A1 | 1/2011 | Pettersson | |
| 2011/0217667 A1 | 9/2011 | Groscurth et al. | |
| 2012/0015329 A1 | 1/2012 | Gross et al. | |
| 2012/0046536 A1 | 2/2012 | Cheung et al. | |
| 2012/0230567 A1 | 9/2012 | Greenberg | |
| 2012/0316486 A1 | 12/2012 | Cheung et al. | |
| 2013/0108979 A1* | 5/2013 | Daon ................... | A61B 5/064 433/29 |
| 2013/0322719 A1 | 12/2013 | Dekel et al. | |
| 2014/0147807 A1 | 5/2014 | Yau et al. | |
| 2014/0236159 A1 | 8/2014 | Haider et al. | |

FOREIGN PATENT DOCUMENTS

| | | |
|---|---|---|
| GB | 2246261 A | 1/1992 |
| WO | 0119273 A1 | 3/2001 |
| WO | 2012068679 A1 | 5/2012 |
| WO | 2013027203 A1 | 2/2013 |
| WO | WO2015048994 A1 | 4/2015 |

OTHER PUBLICATIONS

Notice of Transmittal of the International Search Report and the Written Opinion, ISA, dated Oct. 1, 2014, 25 pages.

CT Scan Protocol, 5-IG-0407, Image Navigation Ltd., Jun. 2008, 16 pages.

Fenlon et al., "Locking acrylic resin dental stent for image-guided surgery", The Journal of Prosthetic Dentistry, vol. 83, No. 4, Apr. 2000, 4 pages.

James E. Eckhart, DDS, "Comparisons of Oral Devices for Snoring", The Journal of the California Dental Assoc., Aug. 1998, 15 pages.

Widmann et al., "In vitro accuracy of a novel registration and targeting technique for image-guided template production", Clin. Oral Impl. Res., Jul. 27, 2004, pp. 6.

Harris et al., "A Combined Corner and Edge Detector", Plessey Research Roke Manor, The Plessey Company PLC, UK, 1988, pp. 147-151.

\* cited by examiner

IMAGE GUIDED NAVIGATION SYSTEM

RELATED APPLICATION

This application is related to and claims priority from U.S. Provisional Patent Application 61/782,255, filed Mar. 14, 2013, the disclosure of which is incorporated herein by reference in its entirety.

FIELD OF THE INVENTION

The present invention relates to a system for facilitating image guided surgery and, more particularly to an improved image guided system for oral surgery.

BACKGROUND

Image guided surgery has had extensive developments over the years and is now a very important tool in surgical procedures. Most of the developments have centered around imaging locations in the body where there is very little access, such as internal organs.

Oral surgery, which is defined herein as any surgery occurring within the oral cavity, can be just as difficult to conduct visually. The oral cavity is relatively small and difficult for a patient to maintain open for prolonged periods of time. Even if a surgical site is visible, once the drill penetrates, it becomes difficult to determine where the tip is at any given time.

Image guided surgery involves the use of a computed or computerized axial tomography scan, commonly referred to as CT or CAT scans, to create a digital image of the surgical site (typically in three dimensions). The surgeon then creates a plan for the surgery using the image. During surgery, the image generated from the prior CT scan is used in conjunction with a special instrument, to visually depict where the tip of the instrument is inside the patient.

In order to do so, the digital image from the scan must be accurately registered to the surgical site of the patient such that movement of the patient causes adjustment of the digital image. The exact location of the instrument tip relative to the patient must also be known.

For oral surgery, such as during dental implant placement, a doctor has to drill in free space while controlling the drill in six degrees of freedom with the patient potentially moving. This makes accurately drilling into good bone while avoiding roots and nerves very difficult. As such, image guided surgery has recently been used to facilitate the drilling process. CT scans of the patient's teeth are used by the doctors to accurately determine bone density, width and height, as well as understand relationships of other teeth and anatomical structures in order to plan a surgical event to provide the restorative solution that would likely be the most successful and least traumatic.

Planning software and fabrication systems exists today that uses the CT image to assist in translating a pre-surgical plan to a passive surgical guide, i.e., creating a virtual plan for the surgery and then prefabricating in the dental laboratory a surgical guide to implement the plan. These passive surgical guides help accurately direct the doctor to the proper location, angle and depth. Passive image guided surgery has limitations. They must be fabricated prior to surgery in a dental lab or by a guide manufacturer. This requires greater doctor and patient time and expense. If there is a change in a patients mouth or the doctor desires to change the plan, the guide is no longer useful. In many cases the patient is unable to open their mouth wide enough to accommodate the instruments needed and the guide.

Active image guided surgery solves many of the problems of passively guided systems, i.e., limited maximal mouth opening, the need to prefabricate a passive guide and the inability to change the plan during surgery can be overcome by actively guided systems. In order to provide active image guided surgery, the position of the patient's mouth, specifically the bone and teeth, must be accurately tracked and registered to the scanned image and the surgical tool. In order to do so, most conventional systems require the creation of a registration device that is attached to the patient's head or inserted into the mouth which includes fiducial markers and a sensor. Some registration devices are attached to the outside of the head, for example, a head mounted fixture. Others involve a fixture that is attached to the jawbone with the sensors located outside the mouth in order to limit the interference with the surgical zone and to permit optical sensors to track the movement of the fixture and surgical tool.

In order to create the oral fixture, an impression is taken, typically of both the upper and lower sets of teeth weeks in advance of the operation. The impression is then sent to a lab where a cast is made substantially duplicating the teeth. From the cast an oral fixture is made that either seats on the teeth or is designed to be drilled into the jawbone. The fixture includes at least the fiducial markers and also, if not fitted with a sensor, includes mounting locations for the optical sensors.

After the lab creates the fixture it is sent back to the dental surgeon. The patient is brought in, fitted with the fixture and a CT scan is taken. The patient is once again sent home. A digital image of the patient's oral cavity is created from the scan and the surgeon develops the surgical plan.

The patient is then brought in for the operation. The fixture is attached to the patient. Optical transmitters are located about the patient and emit signals that are detected by the sensor(s). The sensor(s) send a signal to the software as the patient's mouth moves and an adjustment is made to the digital image of the patient's oral cavity. The software also tracks the position of the instrument and depicts an image of the instrument in the proper location relative to the digital image of the teeth.

In addition to the inconvenience to the patient, existing systems tend to have some difficult accurately registering the patient to the digital scan. All present dental active image-guided surgery systems involve the use of optical tracking which requires that the fixture that is placed in the patient's mouth extends outside the mouth in order to be detected by the optical transmitter or receivers.

SUMMARY OF THE INVENTION

The present invention related to an image guidance system for tracking and depicting movement of a surgical tool during oral surgery. The system includes an oral fixture that is removably attachable to at least one tooth in a patient's mouth. the oral fixture a support made from a rigid material that will not substantially deform when subjected to temperatures of about 100 degrees F. The support includes a base with an inner wall and an outer wall, the inner wall and outer wall extending outward at an angle from the base. The inner and outer walls are spaced from each other a distance that is larger than the width of the tooth to which the oral fixture is intended to be attached. A moldable thermoplastic material is located on an inner surface of the support. The moldable material is configured. upon curing. to retain an impression of the outside contours of a portion of a patient's teeth that were covered by the material. A mount is located on the support for holding a tracking component in an image guidance system.

In an embodiment, the moldable material of the oral fixture is configured to become initially moldable when placed in a liquid bath at an elevated temperature above a mold temperature. The moldable material may provide a visual indication when the material is ready to be molded, such as a change in color of at least a portion of the moldable material.

The support of the oral fixture may include lines of weakening at different points along its length which permit the support to be broken to a desired length for sizing to a particular patient's mouth.

The mount may include or be at least one camera mount that is attached to or formed integral with the support. The camera mount may include at least one camera holder into which a camera may be mounted for viewing a surface in front of or on the opposite side of the mouth from the fixture. The camera holder may be a channel or hole formed in the camera mount that is sized to receive a small video camera. In an embodiment, there are two channels in the camera mount that are positioned to orient two cameras in two different directions relative to the support.

The oral fixture preferably includes a plurality of fiducial markers mounted on the support or in the moldable material for use in determining the location of the oral fixture relative to the patient's teeth. The fiducial markers may be made from a material that has a different radiodensity than the support, the moldable material and the patient's teeth so as to be detectable in a CT scan, for example, but not limited to, metals, such as aluminum or stainless steel, and ceramic. Other materials can be used as would be understood by those skilled in the art. Preferably there are at least three fiducial markers on the oral fixture spaced apart from each other and rigidly attached to the support.

Each fiducial marker may have a radiodensity, size or shape that is different than the other fiducial markers so as to permit the fiducial marker to be automatically detectable by the tracking software. In one embodiment, the fiducial markers are ceramic ball bearings.

An image guidance system is also disclosed for tracking a surgical instrument within the oral cavity. The system includes a plurality of cameras configured to be located within the oral cavity. The plurality of cameras are designed when activated to provide intraoral images of optically visible patterns within oral cavity. A processing system is provided that is programmed to process the intraoral images and recognize patterns so as to triangulate the locations and orientations of each camera. The processing system preferably uses a reference dataset that defines a reference coordinate system that is rigidly aligned to a portion of the oral anatomy. The processing system determines the location and orientation of a tracked instrument based on the reference dataset.

In an embodiment, the optically visible patterns are a visible high-contrast man-made pattern, such as a two-dimensional barcode, which may be located on an appliance that is removably attached to one or more teeth, to the gums, or to the bones in a patient's mouth. In an embodiment, the visible patterns are attached to the tracked surgical instrument.

Preferably at least one camera is attached to the tracked surgical instrument and at least one camera is attached to a dental appliance that is attached to the patient's gums, teeth, or bones within.

The reference dataset may include a location and orientation of an oral fixture with respect to said patient's oral anatomy and that may be part of a CT scan.

In an embodiment, the reference dataset is stored in the processing system. The dental appliance is removably attached to the patient's anatomy at a first location. A second dental appliance is located within the oral cavity at a location so that portions of the second dental appliance are visible from either a camera on the tracked surgical instrument or a camera on the dental appliance. The processing system is programmed to determine a position and orientation of the tracked surgical instrument by combining relative transforms between each camera and the second dental appliance.

In a further embodiment, a first dental appliance includes at least one camera and is removably attached to a location within the oral cavity. A second dental appliance is removably attached to the patient's anatomy of interest at a location where portions of the second dental appliance are visible from camera on the first dental appliance. The tracked surgical instrument includes an optically visible pattern, portions of which are visible from the camera on the first dental appliance. A reference dataset which includes location and orientation data of the second dental appliance with respect to a CT scan, is used by the processing system to determine the position and orientation of the tracked instrument through estimating and combining relative transforms between the camera on the first dental appliance and portions of the pattern on each of the second dental appliance and the tracked instrument.

A method for tracking and depicting movement of an oral surgical tool during oral surgery is also disclosed. The method includes providing an oral fixture with a plastic support with a base and a molded thermoplastic material disposed on an inner surface of the support and molded to certain teeth of the patient that are not teeth being operated on during the oral surgery. A surgical tracking program is provided that receives a CT scan of the patient's mouth with the oral fixture attached to the patient's teeth. Fiducial markers in the CT scan are identified in the program and the scan is stored. A surgical tool is provided with a tool fixture mounted to or part of the tool. A reference fixture is provided at a location that is separate from the oral fixture. The reference fixture includes a reference pattern which provides visual reference points for a video camera to detect and for the program to use in determining the position of the oral fixture and the surgical tool. The program retrieves the stored scan and registers the oral fixture in the patient's mouth to the CT scan. The program determines the movement of the oral fixture by detecting movement of the reference pattern through use of one or more cameras and calculates a corresponding movement of the oral fixture using the tracking program. The program determines the movement of the surgical tool by determining movement of the tool fixture using the tracking program. the program depicts on a display the movement of the surgical tool on the stored scan.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of illustrating the invention, the drawings show a form of the invention which is presently preferred.

However, it should be understood that this invention is not limited to the precise arrangements and instrumentalities shown in the drawings.

DESCRIPTION OF THE PREFERRED EMBODIMENTS

The present invention addresses the prior art deficiencies by providing an image guidance system for efficiently tracking a patient's mouth movement during oral surgery. In one embodiment, the image guidance system includes a plurality of cameras located within the oral cavity to provide intraoral images of optically visible patterns within oral cavity for use in tracking movement of a surgical instrument or tool. A processing system receives and processes the intraoral images to recognize patterns and triangulate the locations and orientations of each camera. The processing system uses a reference dataset which defines a reference coordinate system based on alignment to a portion of the oral anatomy. The processing system determines the location and orientation of the tracked surgical instrument based on the reference dataset. In an embodiment, the system includes an oral fixture that is removably attachable to teeth in a patient and is configured to hold one of the cameras.

Figure 1:
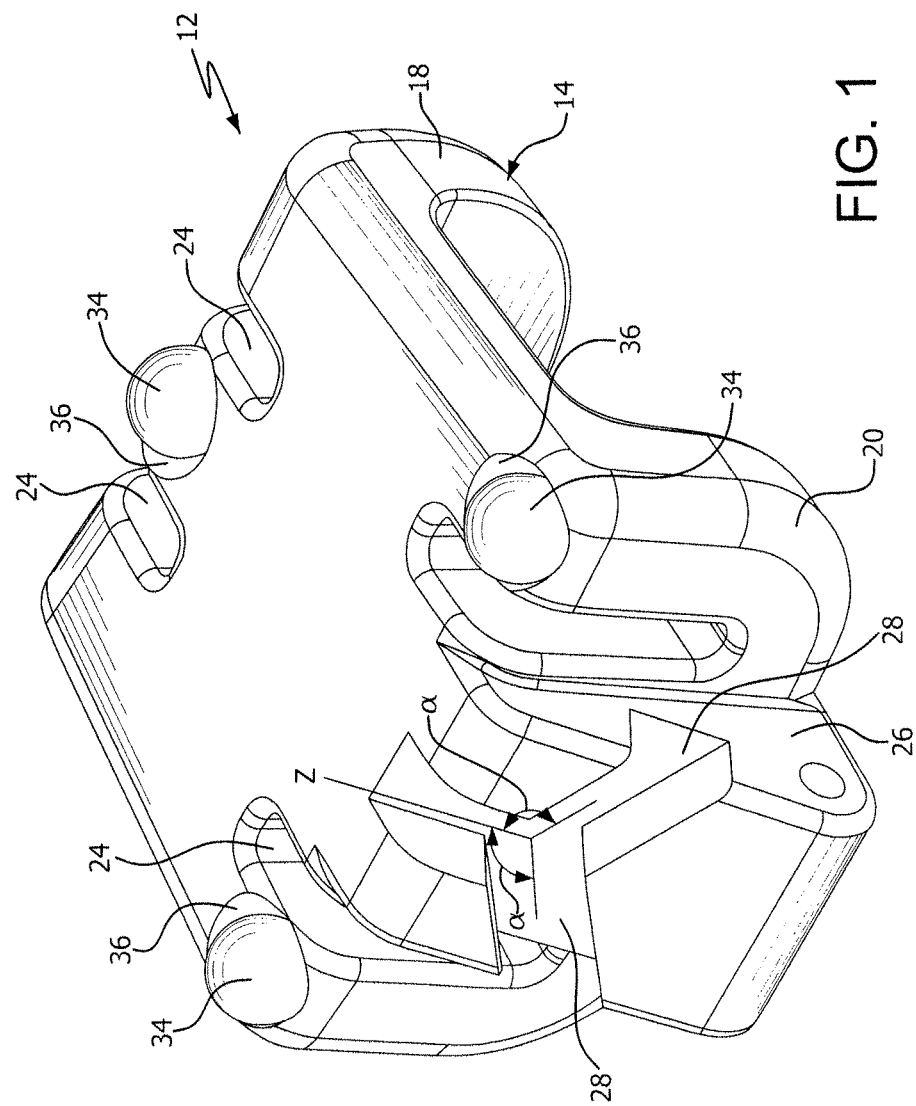
FIG. 1 is a perspective view of an oral fixture according to one embodiment of the invention.
Figure 2:
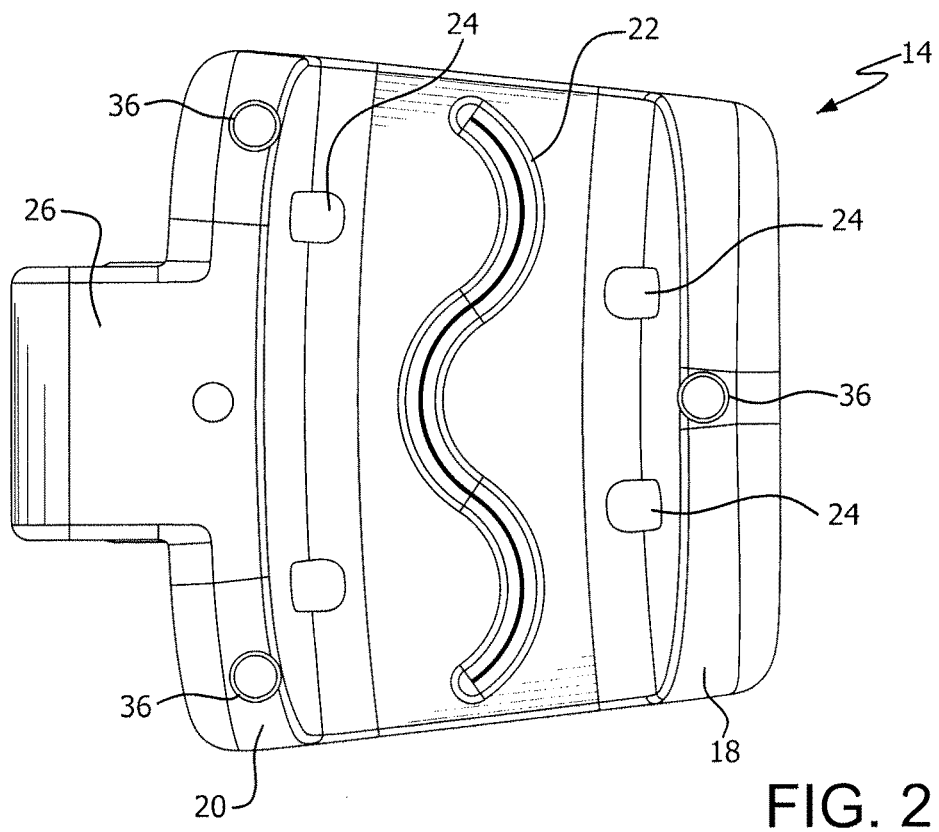
FIG. 2 is a bottom view of the oral fixture of FIG. 1.
Figure 3:
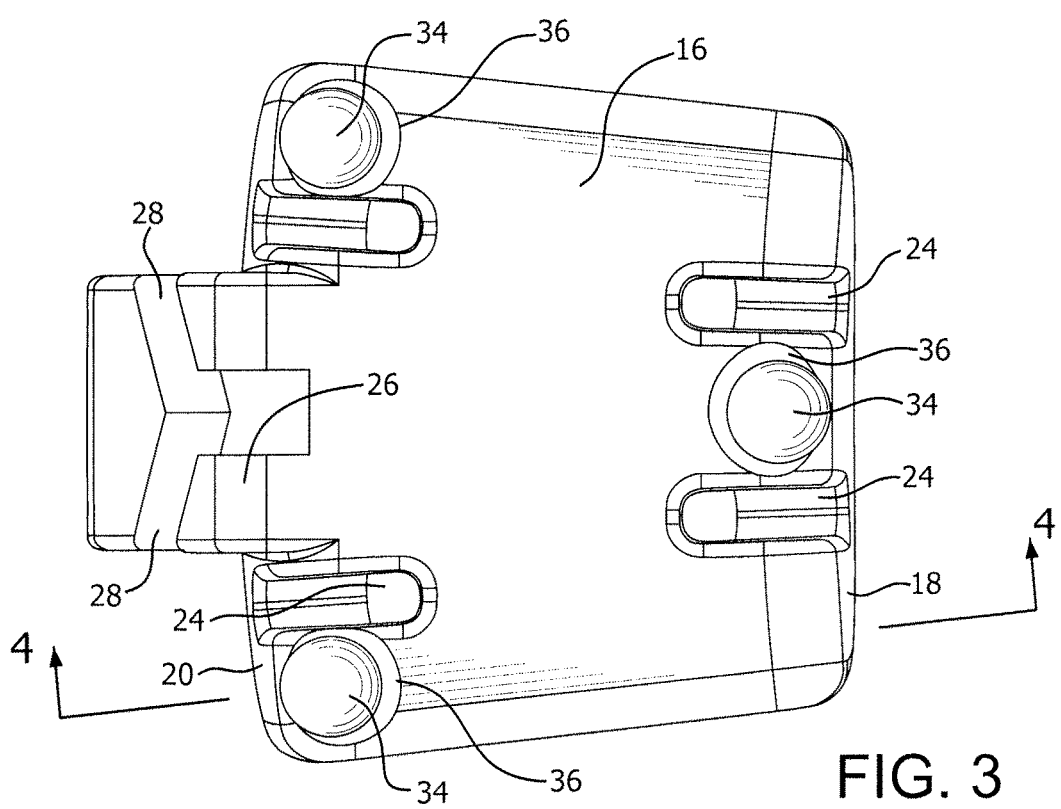
FIG. 3 is a top view of the oral fixture of FIG. 1.

Turning now to the figures, embodiments of the image guidance system 10 are shown. In one embodiment the system 10 includes an oral dental appliance or fixture 12, a tool fixture 100, and a reference fixture 200 (which may be another dental appliance). These fixtures are used in conjunction with tracking software (or a processing system running the software) to provide improved image guidance during an oral surgical procedure. Referring to FIGS. 1-3, a novel oral fixture 12 is shown that is removably attachable to the patient's mouth. More particularly, as shown in the figures, the oral fixture 12 includes a support 14 that is made from a suitably strong material, preferably a thermoset plastic material, that is sufficiently rigid so as not to deform when subjected to the elevated temperatures discussed below. In one embodiment, the plastic material is polyphenylsulphone or acetal copolymer. The support 14 includes a base 16 that is, preferably, generally planar, with an inner wall 18 and an outer wall 20. The inner wall 18 and outer wall 20 are attached to and extend outward from the base 16. Preferably the walls 18, 20 extend outward from the base 16 at substantially or generally right angles from the base 16. However as will be appreciated from the discussion below, the walls could be at other desired angles from the base 16. The walls and base are preferably formed as an integral component. The base 16 and/or walls 18, 20 may include one or more surface irregularities 22, such as protrusions or recesses, that are formed on their inside surface and which assist in securing or attaching an overlying material as will be discussed below. Similarly, holes 24 may be incorporated into the base 16 and/or walls 18, 20 to further secure the overlying material.

The spacing of the inner and outer walls 18, 20 is larger than the width of the teeth to which the oral fixture 12 is intended to be attached. It should be readily apparent that the spacing of the walls 18, 20 can be different between fixtures designed for adults and children. The walls 18, 20 preferably have a height from the base which extends below the top of the patient's teeth when installed. Preferably the height is sufficient to extend about 10 mm to about 13.5 mm down from occlusal surface when installed on a patient's tooth with the overlying material.

The oral fixture 12 also includes at least one mount 26 attached to or formed integral with the support 14. The mount is configured to attach a tracking component to the oral fixture for use in an image guidance system. In one embodiment, the mount is configured to receive one of more cameras for use in tracking as discussed below. It is also contemplated that the mount can be used to attached a reference plate to the support as will become more apparent below. In the illustrated embodiment a camera mount 26 is shown formed integral to the outer wall 20 and projects outwardly therefrom. As will become evident, the camera mount 26 also acts as a handle to facilitate placement and removal of the oral fixture 12 from a patient's teeth. The camera mount 26 includes at least one camera holder 28 into which a camera may be mounted. The camera holder 28 is configured so as to hold a camera in a direction to view a surface in front of or on the opposite side of the mouth from the oral fixture 12. In the illustrated embodiment, the camera holder 28 is a channel or hole formed in the camera mount 26 that is sized to receive a small video camera. The camera holder 28 also is configured to permit a wire that is attached to the camera to extend out of the support and attach to a computer or other recording device as will be discussed below. The camera holder may alternatively be a clip, clasp or other device suitable for securing a camera to the support 14.

Figure 4:
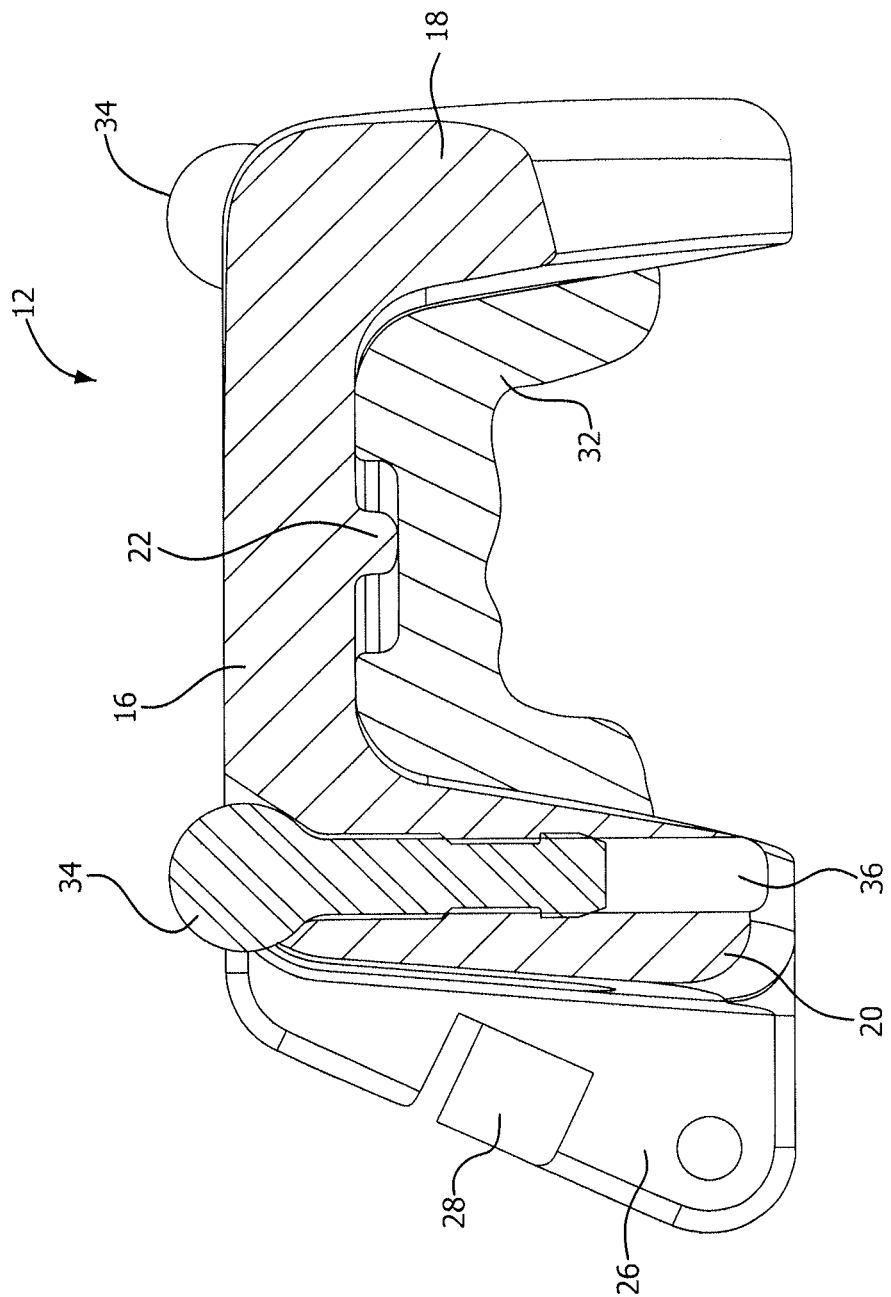
FIG. 4 is a cross-sectional view of the oral fixture taken along lines 4-4 in FIG. 3 illustrating the molded material with an impression formed in it.

In order to provide a versatile oral fixture 12, it is contemplated that the camera mount 26 may include more than one camera holder 28. As shown in FIGS. 1-3 and 4A, in the illustrated embodiment there are two channels 28 in the camera mount 26 that are positioned to orient cameras 30 in two different directions relative to the support 14. Preferably the directions are at an angle α on either side of a vertical access Z as shown in FIG. 4A. Angle α is preferably between 5 and 45 degrees from the vertical access Z, and more preferably is about 30 degrees. This configuration permits the oral fixture 12 to be used with either the top or the bottom teeth of a patient, and on either side of the mouth. If there is only one camera holder 28 in the camera mount 26, it can be formed in the mount 26 to orient the camera at any angle between 0 degrees to about 45 degrees to the vertical axis Z.

As shown in FIG. 4B, the oral fixture 12 also includes a moldable thermoplastic material 32 located on an inner surface of the support 14, preferably on the base 16. The moldable material 32 is designed to form an impression of a portion of a patient's teeth. More specifically, when the moldable material is in its uncured (unset) state, the material is "activated" by placing the oral fixture 12 (support 14 with moldable material 32 on it) into a bowl of warm or hot water that is at a temperature above which the material begins to become moldable. Preferably the chosen material has a characteristic that provides the user with a visual indication that the material is ready to be molded, such as changing color (e.g., from white to clear or translucent). Once the material 32 is activated, the oral fixture 12 is placed on a patient's teeth and slight downward pressure is applied causing the moldable material 32 to deform around the top and at least some of the sides of the teeth between the support walls 18, 20. After a prescribed period of time, generally about 30 seconds to one minute, the moldable material sets to form an impression of the outside shape and contours of the teeth that were covered by the material. The oral fixture 12 can then be removed from the patient's mouth. Further curing can be achieved by placing the oral fixture 12 with the mold material into a bowl of cold or ice water to complete the setting process.

The material selected must remain solid (cured) at temperatures typically existing in a person's mouth (generally, around 100 degrees F.), and moldable at a temperature above that (e.g., above 130 degrees F.), at least until it is initially set. The material should be sufficiently rigid in its cured state so as to maintain the shape of the impression without distorting. Suitable thermoplastic materials 32 for use in the invention includes Polycaprolactone or Polyvinylsiloxane (PVS). However, any type of moldable material that can set and retain an impression can be used in the present invention. The moldable material 32 may be flavored to please the patient during the molding process. The amount of material used will vary depending on the number and size of teeth that are to be molded.

It has been determined that the oral fixture 12 and moldable material 32 can be small enough to cover two or three teeth and still provide a secure attachment of the oral fixture 12 to the patient's teeth. If properly molded, it may be possible to use an even smaller size fixture, thus minimizing discomfort to the patient. The oral fixture 12 and moldable material 32 may be sized for different mouth sizes (e.g., adult, teen, children). It is also contemplated that the support 14 can be designed in a large size with lines of weakening at different points along the length which permits the support to be broken at the desired length. Such a configuration would allow the doctor to size the oral fixture 12 more easily to the patient's mouth. As will be apparent from the discussion below, the support 14 is not intended to hold the fixture 12 to the teeth. Instead, the moldable material 32 provides the retention of the oral fixture 12 to the teeth. Thus, there should be a sufficient amount of moldable material 32 to retain the oral fixture 12 on to the teeth.

As discussed above, the support 14 preferably includes surface irregularities 22 and/or holes 24 formed in the base 16 and/or walls 18, 20 which facilitate the attachment of the moldable material 32 to the support 14. As the moldable material is being formed, the material flows through or into the holes 24 and around the irregularities 22, thereby providing a more secure attachment to the support 14.

The oral fixture 12 also includes a plurality of fiducial markers 34 mounted on the support 14 in order for the system to determine where the oral fixture 12 (and thus the camera) is relative to the patient's teeth. The markers 34 are at certain locations on the fixture 12 and are part of a registration system for properly locating the fixture 12 in space. As will be discussed in more detail below, the fiducial markers are detected during a CT scan of the patient's mouth and their location is registered in the scan. There are preferably at least three fiducial markers 34 spaced apart from each other and rigidly attached to the support 14. The use of the three fiducial markers permits location of oral fixture in three dimensions. The fiducial markers may be located on the base 16 and/or the walls 18, 20. As shown in FIGS. 1-3, the support 14 includes marker mounts 36 which may be holes or indentations formed in the support 14 and are designed to receive the fiducial markers 34.

The fiducial markers 34 may be spherical in shape and/or colored so as to be easily detected by a technician or doctor, as well as the software being used. More specifically, in order for the fiducial markers 34 to be detected in a scanned image, the fiducial markers 34 must have a different radiodensity (i.e., the density that is detected by the CT scan) than the fixture, moldable material and teeth. In one embodiment, the fiducial markers 34 are ceramic ball bearings. However, other materials, shapes and sizes may be used. Preferably the fiducial markers 34 each have their own radiodensity or are of different sizes or shapes so that a software program can be used to automatically detect the different fiducial markers 34 in the scanned image. The software may also apply a color in the scanned image that corresponds to the markers color or shape to assist in registration of the oral fixture 12 as will be discussed further below. It is also contemplated that the fiducials can include passive optical attributes, such as specular or diffuse surfaces, or active optical attributes, such as light emitting materials, for use in visually locating the fiducials relative to a camera or other location.

While the preferred fiducial markers are distinguished from the teeth and oral fixture 12 by their radiodensity, it is also contemplated that other distinguishing features can be used other than density. For example, the markers can be pre-fixed transmitters or other position location devices.

Figure 5:
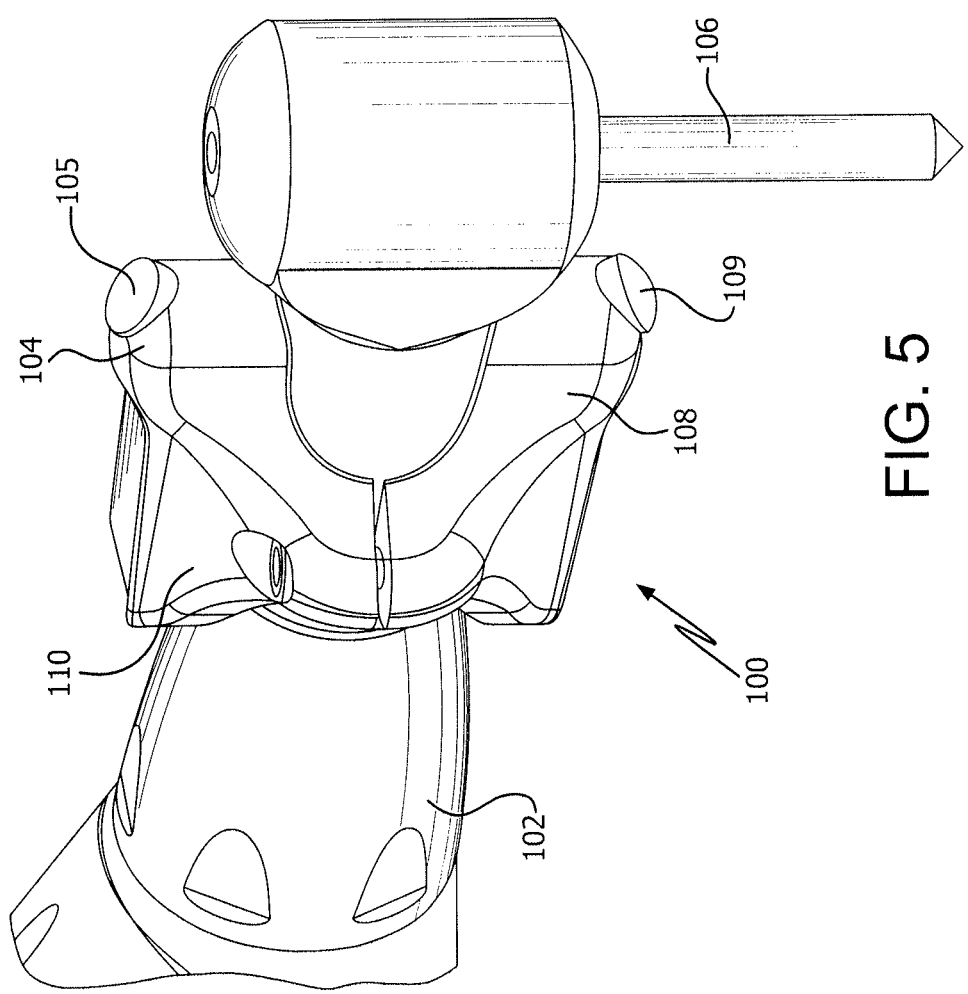
FIG. 5 is a perspective view of a tool with a tool fixture according to an embodiment of the present invention.
Figure 6:
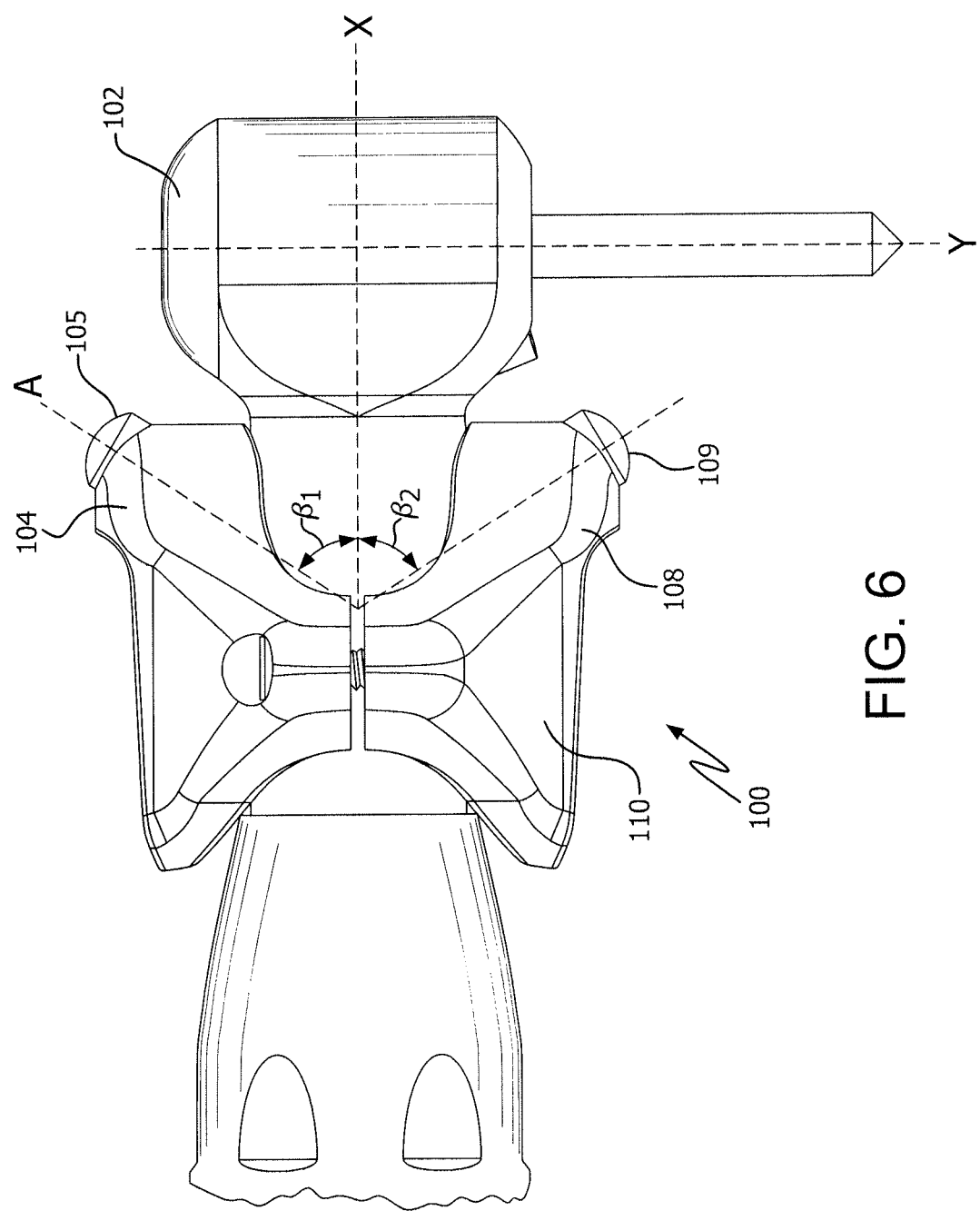
FIG. 6 is a side view of the tool and tool fixture of FIG. 5.

Referring now to FIGS. 5 and 6, a tool fixture 100 according to one embodiment is shown. The tool fixture 100 is mounted to or part of a dental surgical tool 102, such as a drill. The tool fixture 100 preferably includes at least one tool camera mount 104 for securing and positioning a camera relative to the tool 102. The tool camera mount 104 is preferably configured to orient the camera 105 so as to detect a surface that is not where the tool 102 is to be operating on. That is, the tool camera mount 104 angles the camera away from the drilling or operating location. As shown in FIG. 6, the tool camera mount 104 has an axis A that is at an angle $\beta_1$ to an axis X running long the axis of the tool 102. As will be discussed below, this permits a camera mounted in the tool camera mount 104 to detect a reference location in another part of the mouth.

The tool fixture 100 may include a second tool camera mount 108 for positioning a second camera 109 relative to the tool 102. The second tool camera mount 108 is preferably configured to orient the second camera 109 so as to permit viewing of the tool bit 106 and/or the area being operated on. As shown in FIG. 6, the second tool camera mount 108 is preferably at about a 90 degree angle to the first tool camera mount 104 or at an angle $\beta_2$ to the axis X. In one embodiment, $\beta_1$ is preferably between about 10 and about 90 degrees, depending on the position of the camera and the field of view, and more preferably about 60 degrees. $\beta_2$ is preferably between about 20 and about 90 degrees, and more preferably about 60 degrees.

In the illustrated embodiment, the tool fixture 100 is attached to the tool 102 through a clamp 110 to prevent the camera from moving relative to the tool. However, it is also contemplated that the tool fixture 100 may be formed integral with the tool 102.

Figure 7:
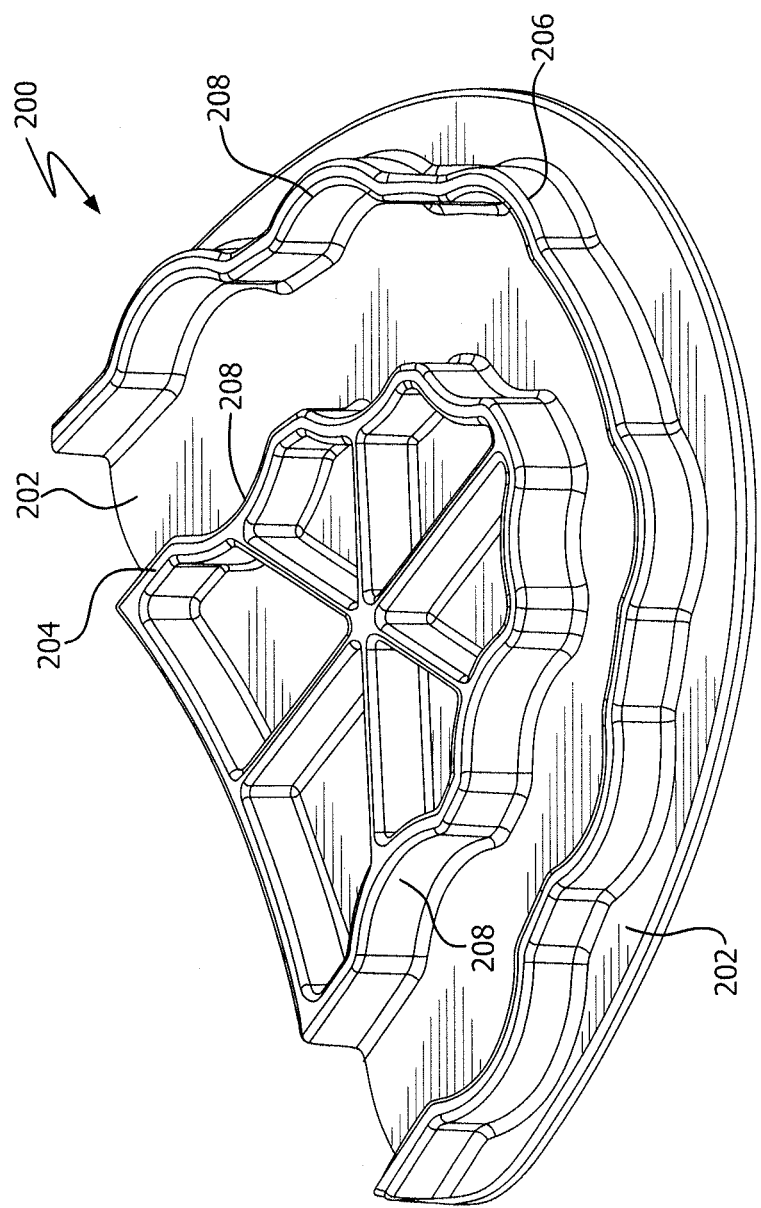
FIG. 7 is a perspective view of a reference fixture according to one embodiment of the present invention for use with an upper set of teeth.
Figure 8:
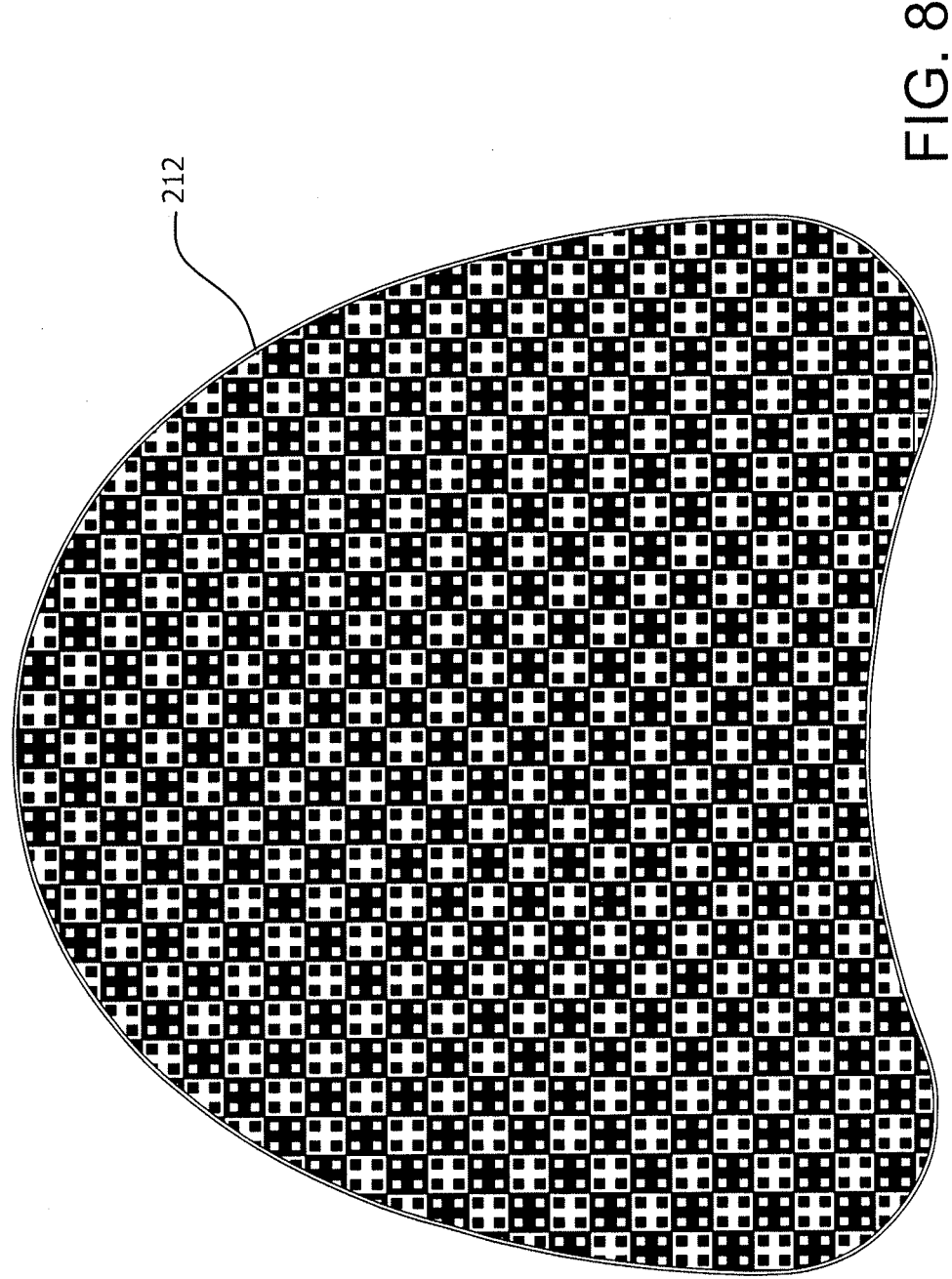
FIG. 8 is a bottom view of the reference fixture of FIG. 7 illustrating a graphical representation of a reference pattern.
Figure 9:
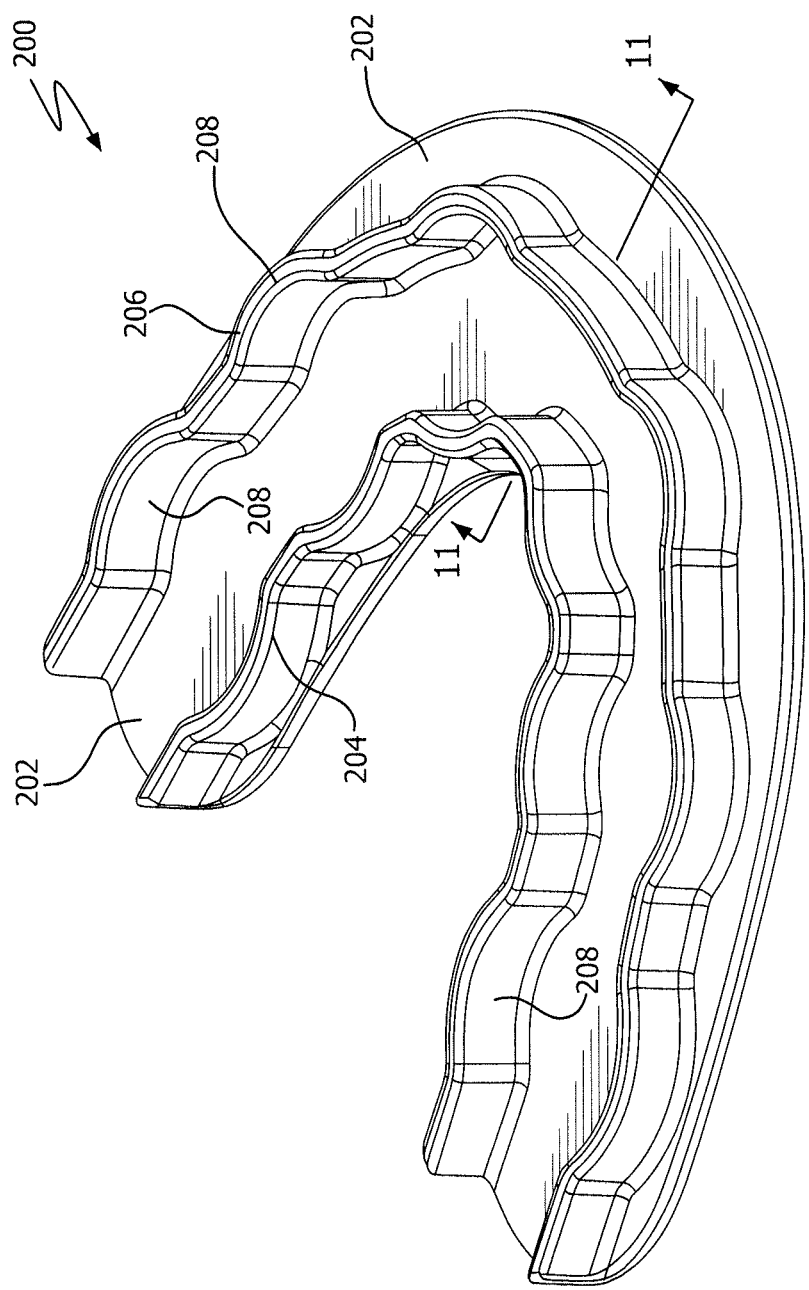
FIG. 9 is a perspective view of a reference fixture according to another embodiment of the present invention for use with a lower set of teeth.
Figure 10:
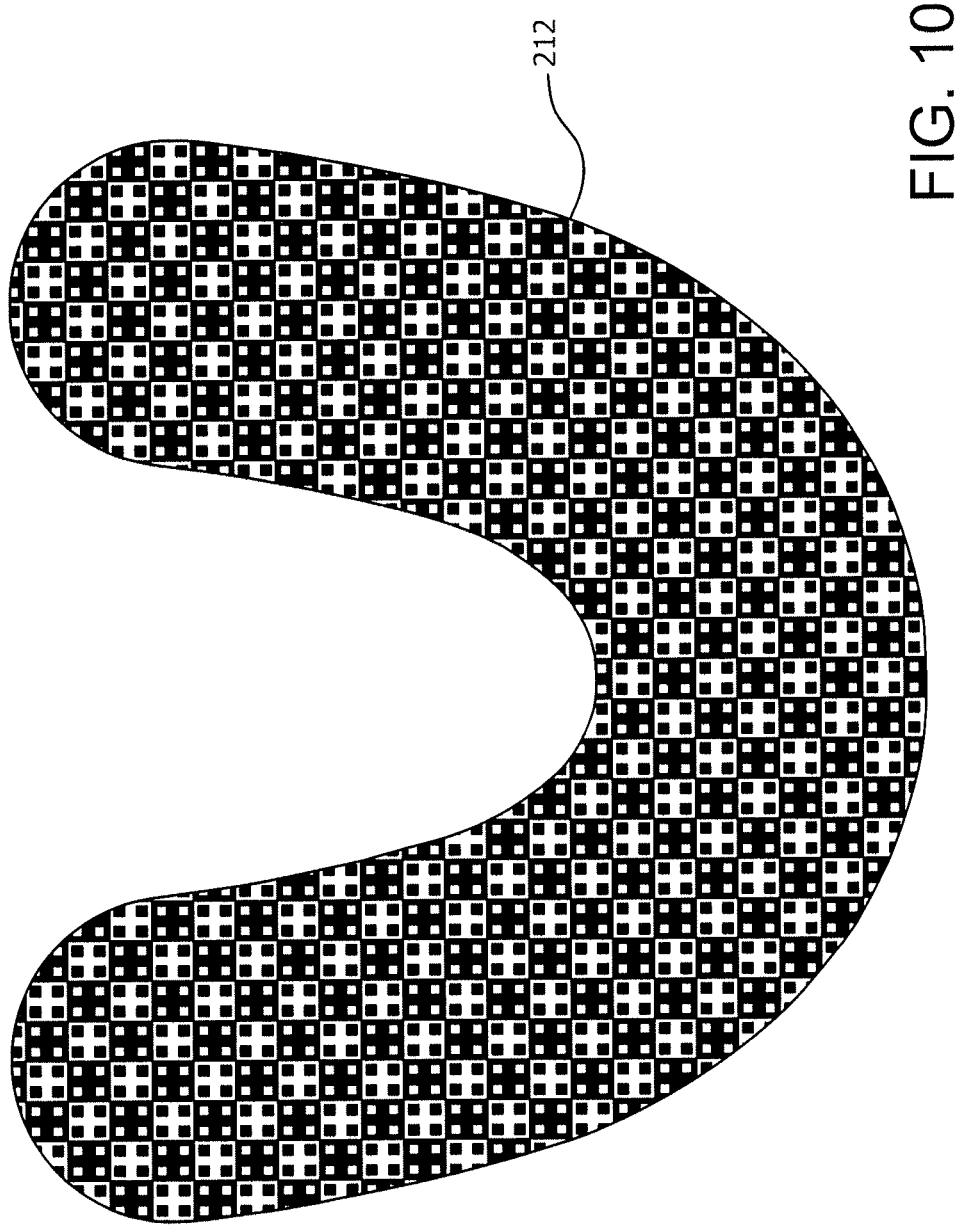
FIG. 10 is a top view of the reference fixture of FIG. 9 illustrating a graphical representation of a reference pattern.

Referring now to FIGS. 7 and 8, a reference dental appliance or fixture 200 according to one embodiment is shown for use with a lower set of teeth in a patient. FIGS. 9 and 10 illustrate a second embodiment of the reference fixture 200 for use with a upper set of teeth. in one embodiment, the reference fixture 200 includes a base plate 202 with inner and outer raised edges 204, 206 formed integral with and extending outward from the base plate 202. As with the oral fixture 12, the reference fixture 200 may include one or more surface irregularities (not shown), such as protrusions or indentations, formed on the base plate 202. The raised edges 204, 206 preferably also include surface irregularities 208, such as indentations as shown. The reference fixture 200 is preferably made from the same or similar material as the camera support 14 since it is also designed to be attached to the patient's teeth using a moldable material. Specifically, referring to FIG. 11, a moldable material 210, preferably similar to the moldable material 32 in the oral fixture 12, is disposed on the base plate 202 between the edges 204, 206. The application, forming and setting of the moldable material 210 is similar to the moldable material 32 described above and, thus, no further discussion is needed.

Figure 8A:
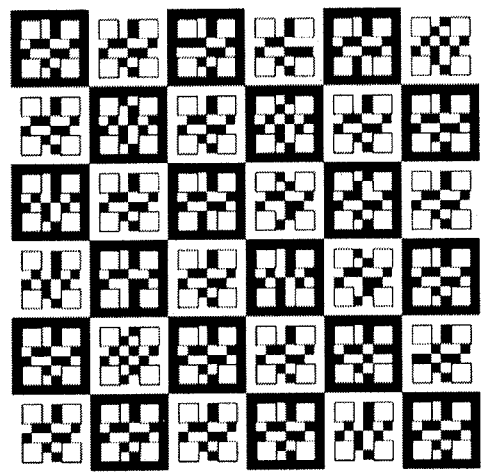
FIG. 8A is a graphical illustration of another reference pattern useful in the present invention.
Figure 8B:
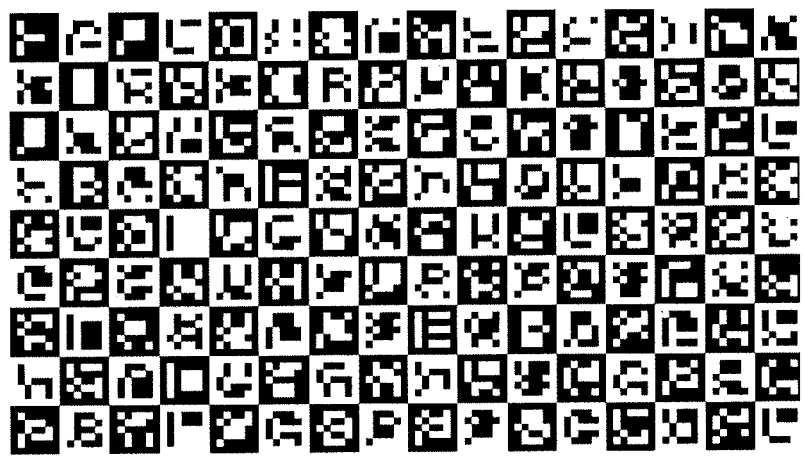
FIG. 8B is a graphical illustration of yet another reference pattern useful in the present invention.
Figure 8C:
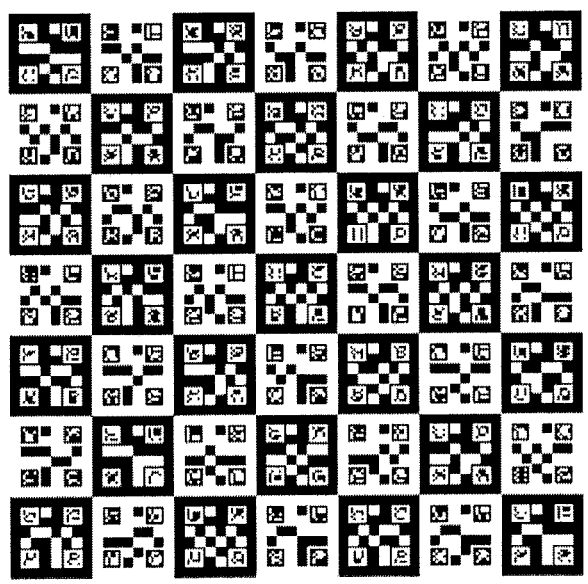
FIG. 8C is a graphical illustration of a further reference pattern useful in the present invention.
Figure 11:
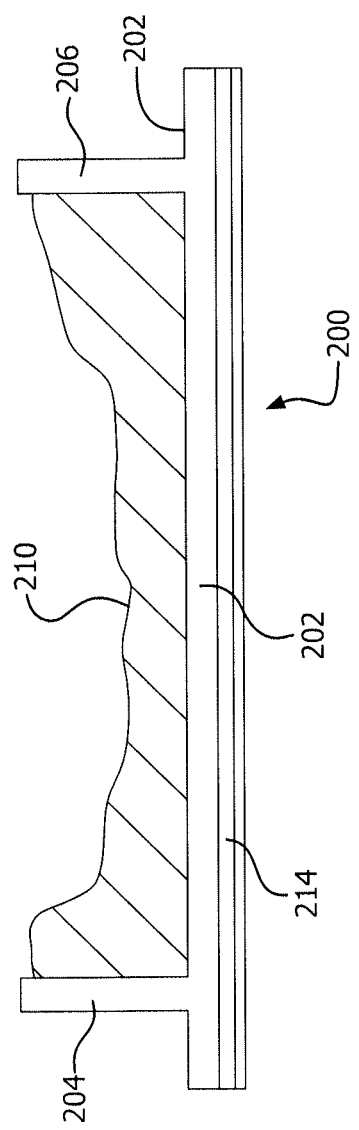
FIG. 11 is a cross sectional view of the reference fixture of FIG. 9 taken along lines 11-11 with a moldable material on it.

A reference pattern 212 (generically depicted in FIGS. 8 and 10) is formed on the outer surface of the reference fixture (opposite from the side with the moldable material 210). The reference pattern 212 is an optically visible pattern that is configured to provide visual reference points for the video cameras to detect for use in determining the position of the cameras in the mouth. In the illustrated embodiment, the reference pattern is preferably a series of non-repetitive Quick Reference or QR Codes spaced across the outer surface. See, for example, FIGS. 8A, 8B and 8C which depict images of non-repetitive reference patterns that may be used in the present invention. Bar codes, Aztec codes or other 2D codes, or graphical images, could also be used. The pattern preferably uses contrasting colors, such as black and white, to facilitate detection and recognition by the system. In particular, FIG. 8C depicts a two-scale pattern. The pattern is a 2D barcode, which is made up of a barcode-within-a-barcode allowing detection at multiple scales. The larger checkerboard squares are uniquely identifiable from a larger distance, while the four smaller tiles in each corner of the larger tile are detectable by a camera placed much closer to the reference fixture. This, along with the fact that the ranges of the larger and smaller patterns overlap, allows the camera to detect the reference fixture over a much wider range of aspect and distance. Also it is contemplated that other mechanisms can be used to provide the reference data needed, including LEDs, a data matrix, data glyphs, or raised or lowered features similar to braille. The fiducials can be balls with reflective surfaces for use in calibrating where the camera or pattern is related to the fiducials. Flashes of light can be sent toward the fiducials and the reflected light captured by the camera for determining the fiducials locations. As will become apparent, the use of the reference pattern is for purposes of determining movement and location of the cameras. As shown in FIG. 11, the reference pattern 212 may be formed on a layer of material 214 that is adhered to the outer surface of the reference fixture. Alternatively, the pattern may be molded or etched onto or disposed directly on the reference fixture 200.

It is contemplated that the reference plate 200 may be configured to provide backlighting or other mechanism to increase the contrast of the reference pattern 212 to facilitate detection. If the reference plate is backlit, the reference pattern 212 is preferably at least partially made from transparent or translucent material so as to enhance the contrast. It is also contemplated that a fluorescent material can be used to facilitate detection.

The following describes a preferred system for position tracking of a drill or other tool during image guided dental surgery according to the present invention and using the oral fixture 12, tool fixture 100 and reference fixture 200 described above.

A patient is first fitted with the oral fixture 12 and the reference fixture 200. The doctor selects a properly sized oral fixture 12 or adjusts the size of the oral fixture 12 by breaking the support 14 along one of its lines of weakening. The oral fixture 12 with the unmolded material 32 is placed into a warm water bath. The warm water (or other non-toxic solution) softens or activates the moldable material 32, making it more compliant. As described above, in one embodiment, the moldable material 32 is selected so as to change color or otherwise provide an indication when it is sufficiently moldable for application. For example, the moldable material may be white in its static or cured condition, but turns clear/translucent when heated up to a temperature that makes it sufficiently moldable. It is anticipated that placing the oral fixture 12 in warm or hot water (e.g., above 130 degrees F.) for approximately 1-2 minutes should be sufficient to soften the preferred material.

The oral fixture 12 is then applied to the teeth of the patient. Preferably the oral fixture 12 is applied to teeth in the patient's mouth that are not the ones where the surgery is to take place. For example, if the surgery is to take place on the molars on the right side of the mouth, the oral fixture 12 is preferably attached to teeth on the left side of the mouth so as not to interfere with the surgical procedure.

The doctor or technician applies pressure on the support 12 toward the teeth. The doctor or technician can use their fingers to assist in molding or conforming the moldable material 32 to the contours of the teeth. After the material is adjusted to conform to the teeth, it is left in place to permit a sufficient amount of curing in order to maintain the impression in the moldable material 32. The amount of time will vary depending on the type of curable material used. However, for a number of materials the molding process will be sufficiently complete in about 30 seconds to 1 minute. This may be detected by a change back toward the original color of the material (e.g., a change from clear to white).

The oral fixture 12 is removed by grasping the support and/or camera mount and lifting the oral fixture 12 off the teeth. At this point the moldable material 32 will have an impression defining the outer contours of the teeth that were molded. The moldable material 32 is then allowed to cure completely, such as by allowing it to sit. To expedite the curing process, the fixture can be placed in cold or ice water for several minutes.

If the oral fixture 12 does not include the fiducial markers 34, they are then attached to the support, such as with adhesive or threaded into the holes 36. However, it is preferred that the fiducial markers 34 are pre-attached to the oral fixture 12.

The oral fixture 12 is then placed back in the patient's mouth on the same teeth that were molded. The molded impression of the teeth will lock the oral fixture 12 onto the teeth. A CT scan is taken of the patient's mouth, or at least the portion of the mouth of interest. The CT scan captures the location of the fiducial markers 34 since they are located on the oral fixture 12. The oral fixture 12 is then removed and stored for the surgical operation.

The scanned data is imported into or used by a surgical planning and tracking program. The program is preferably configured to automatically detect the fiducial markers 34, such as by their specific radiodensity, and may assign them specific colors or alphanumeric identifiers.

The doctor reviews the scanned image to determine a surgical plan. The plan may be depicted on the image, such as with notes or directional indicators, e.g., a colored line indicating the path that the surgical tool should follow to get to the site of interest. The plan may be stored in the program.

In order to provide proper location of the camera on the oral fixture, the present invention uses the location of the fiducial markers 34 on the oral fixture 12 to calculate the camera location. This can be done on the day of surgery or prior to the surgery. A camera 30 is inserted into the appropriate camera holder 28 in the camera mount 26. One embodiment of the invention uses a Medigus Introspicio 110 3.0 mm camera. The camera 30 is connected to a computer and the surgical planning and tracking software program is activated. The oral fixture 12 is held up to a reflecting surface, such as a mirror, in multiple orientations and the software computes the location and orientation of the fiducial markers 34 on the oral fixture 12 relative to the camera 30 and stores the information.

Alternatively, the fiducials detected in the CT may be a different set than those detected optically, in which case there is no need to hold the oral fixture up to a mirror.

Figure 20:
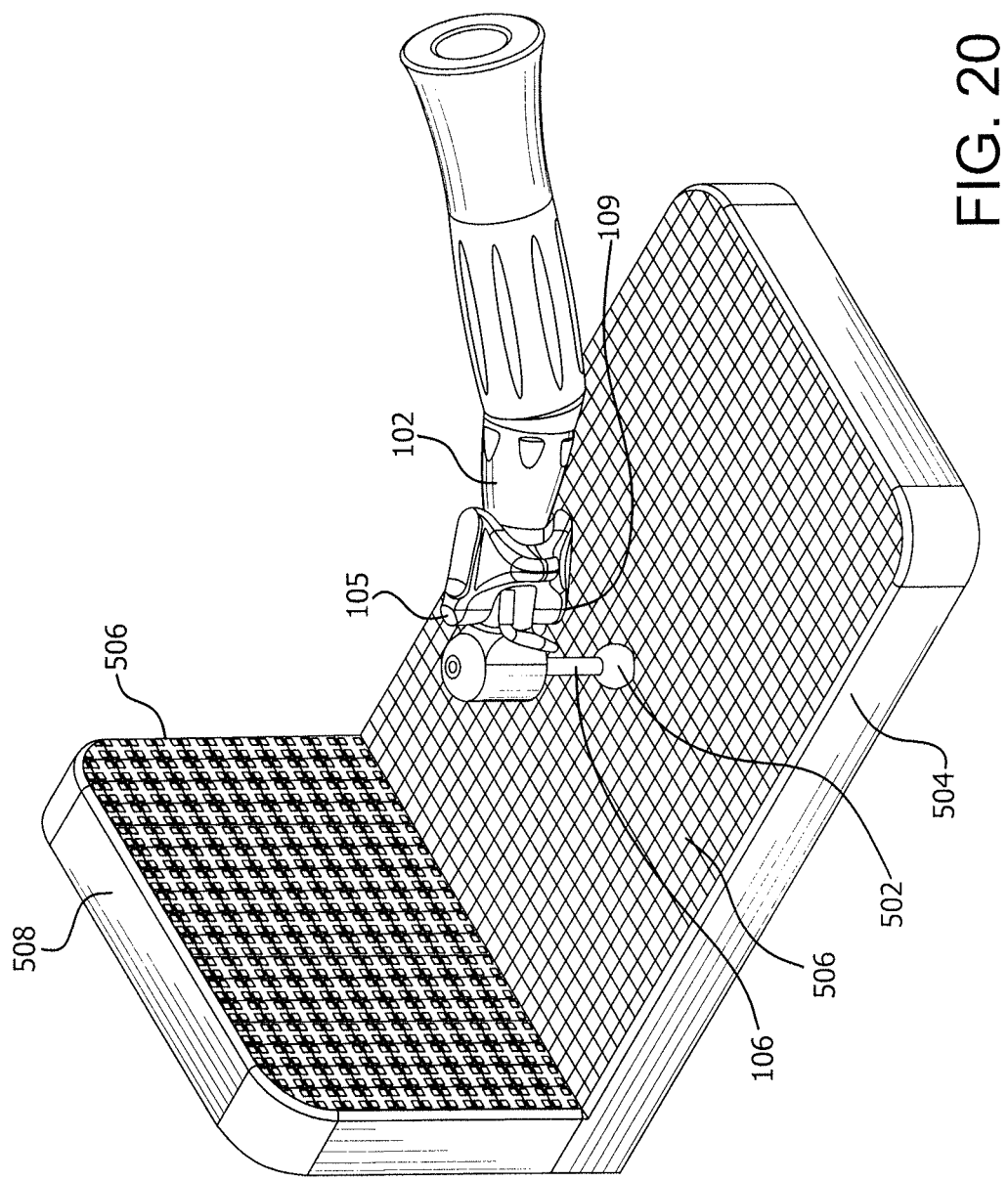
FIG. 20 illustrated an embodiment of a registration device for registering a tool and tool bit.

In lieu of optical fiducials, it is contemplated that a pivot calibration method can be done with three separate (non-collinear) pivot points. The pivot points could be spheres that a cupping tool may pivot about, indentations that a spherical tool could pivot within, or tapped holes that a sphere-tipped pivot tool could be screwed into. This method of calibration is described below in more detail with reference to FIG. 20.

When it is time for the surgical procedure to be conducted, the oral fixture 12 is reattached to the same teeth in the patient's mouth with the camera 30 in place. The camera is connected to the computer system where the surgical tracking software program is running. The wire transmits video data from the camera 30 to the computer system for providing position data of the camera 30, and thus the oral fixture 12.

The patient is next fitted with the reference fixture 200. The doctor selects a properly sized reference fixture 200. The reference fixture 200 with the unmolded material 210 is placed into a warm water (or other non-toxic solution) bath. The warm water softens or activates the moldable material 200, making it more compliant.

The reference fixture 200 is then applied to the teeth of the patient on the opposite set of teeth than the ones being operated on. Thus, if the surgery is to be performed on the upper teeth, the reference fixture is applied to the lower teeth. The doctor or technician applies pressure on the base plate 202 toward the teeth. Again, the doctor or technician can use their fingers to assist in molding or conforming the moldable material 210 to the contours of the teeth. After the material is adjusted to conform to the teeth, it is left in place to permit a sufficient amount of curing in order to maintain the impression in the moldable material 210. The amount of time once again will vary depending on the type of curable material used.

Figure 12:
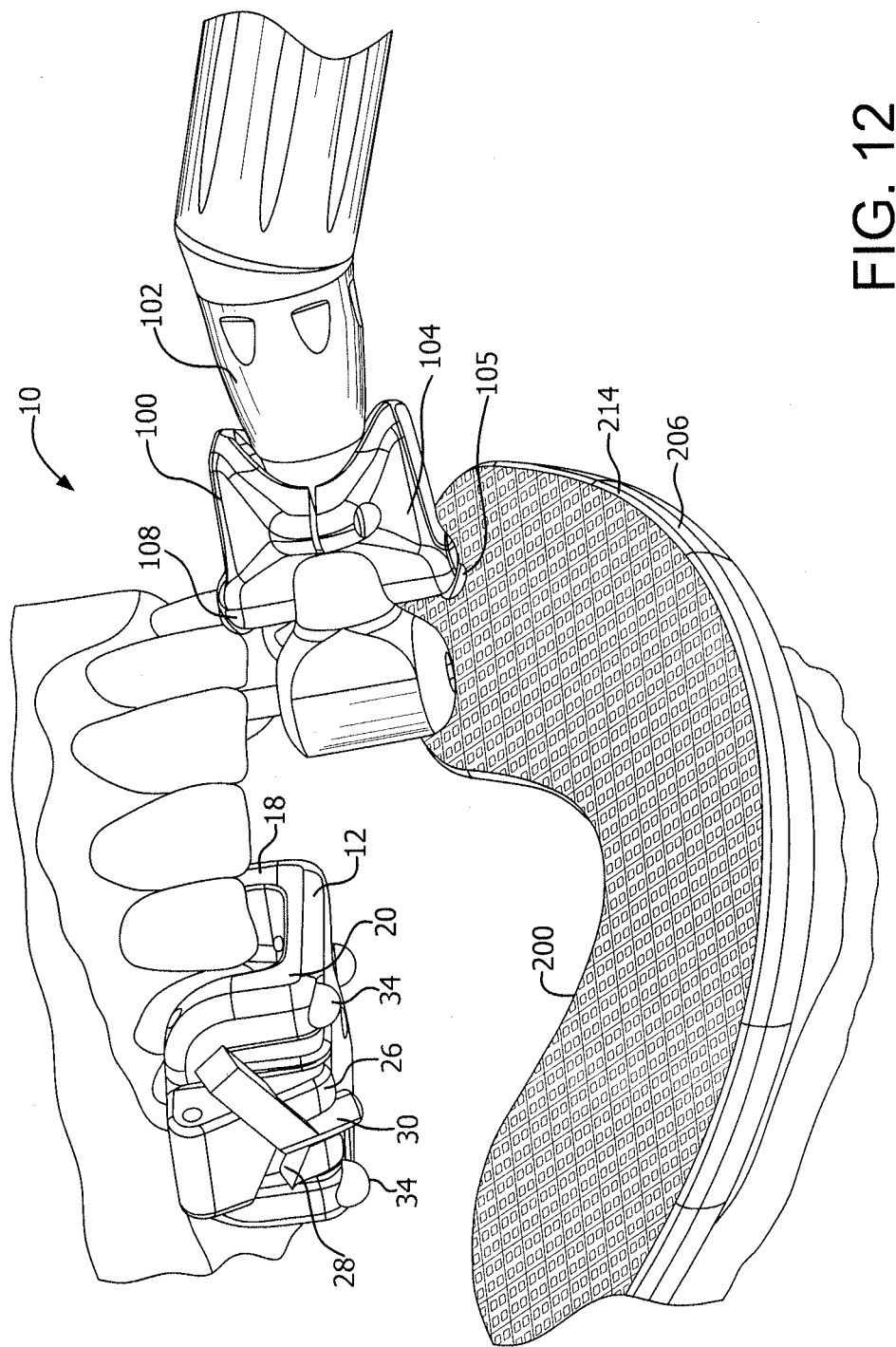
FIG. 12 is a representation of the oral fixture, reference fixture and tool fixture in use in a patient's mouth according to one embodiment of the invention.

If the reference fixture 200 does not include the reference pattern 212, a layer of material 214 that includes the pattern is applied to the outer surface of the base plate 202, preferably prior to attachment to the patient's teeth. The reference pattern 212 provides image reference data that is captured by the camera 30 and relayed to the software during use for determining the movement of the camera 30 and, thus, the oral fixture 12. FIG. 12 depicts the oral fixture 12 and reference fixture 200 attached to a patient's teeth with a tool fixture 100 in position to conduct surgery.

In one embodiment of the invention, the system permits the surgeon or technician to manually correlate or register the prior CT scan to the current position of the mouth. This is accomplished by registering the location of the actual fiducial markers 34 to the imaged markers. The system preferably requests that the doctor or technician begin the registration by touching a sensor device that is connected to the system to each of the fiducial markers 34 on the actual oral fixture 12. The sensor device can be a pointer. The sensor device transmits the position of each fiducial marker 34 to the program (either wirelessly or through a wired connection).

The program guides the doctor/technician to register the oral fixture 12 by directing them to touch each fiducial marker 34 in a predetermined manner. For example, in a configuration where the markers are colored, the program may direct the doctor/technician to "touch the green fiducial marker". The corresponding fiducial maker in the previously scanned imaged data would be depicted on the screen with a green color. When the doctor/technician touches the correct marker 34 on the oral fixture 12 and hits "enter", the program correlates the actual fiducial marker 34 to the scanned fiducial marker in the imaged dataset. The program then directs the doctor/technician to touch the next marker and so on.

Instead of requiring the doctor or technician to hit enter or some other key when the position sensor is in place, it is contemplated that the sensor device could include a pressure sensor. When the doctor or technician presses down on the fiducial marker, the sensor device automatically sends the data to the program.

Alternately, it is preferred that the system automatically correlates or registers the prior CT scan to the current image. This is accomplished by the program using the tool camera to detect the location of the fiducial markers 34 on the oral fixture 12. The program orients the fiducial markers 34 in the CT scan to align with the markers 34 detected by the camera. Thus, the software handles the automatic orientation of the CT scan to correlate with the actual video data retrieved from the cameras.

Once the CT scan is oriented to the actual video data, the tracking of the actual movement of the oral fixture 12, as determined from the camera image data, and, thus, movements of the patients mouth (in three dimensions) can be correlated to and depicted on the previously scanned CT image so that the actual movement of the patient's mouth will produce corresponding movement of the scanned image of the patient's mouth on the computer screen. The actual movement of the oral fixture 12 is determined by the camera 30 on the oral fixture 12 transmitting the image of the reference pattern 212. Using the image of the reference pattern 212, and stored data of the location of the actual fiducial markers 34 on the oral fixture 12 relative to the camera 30, the program can calculate the actual movement of the oral fixture 12. Such calculations and programming techniques are well known and, thus, no further information is necessary.

The program is also configured to receive position data of the surgical tools that are being used. Specifically, as discussed above, the tool fixture 100 is attached to or formed integral with the tool 102. A camera 105 is attached to the camera mount 104 on the tool fixture 100. When the tool 102 is positioned within the mouth the camera 105 is mounted so that it is oriented toward the reference pattern 212 on the reference fixture. As with the oral fixture, the camera 105 on the tool fixture 100 relays the image of the reference pattern 212 to the software program. Using the image of the reference pattern 212, and stored data of the location of the camera 105 on the tool 102, the program can calculate the actual movement of the tool 102.

Figure 13:
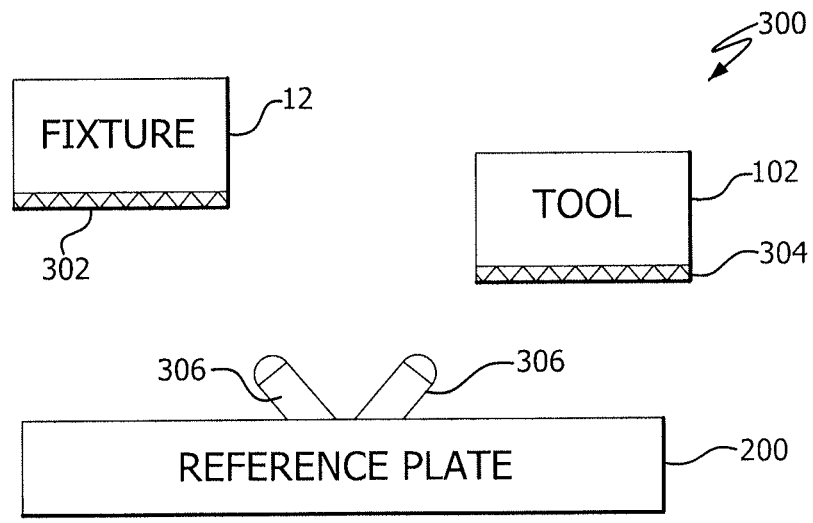
FIG. 13 is a schematic representation of an alternate embodiment of the present invention using an oral fixture, a reference fixture and a tool with a different arrangement of cameras and reference patterns.

While the above discussion involved the use of a video tracking system that includes cameras mounted to the oral fixture and the tool fixture in combination with a reference plate, other arrangements are also contemplated. For example, in one alternate embodiment 300 shown in FIG. 13, the oral fixture 12 does not include a camera and camera mount but is otherwise constructed similar to the prior embodiment and mounted to a patient's teeth or secured to the bone as discussed above. The oral fixture 12 includes a fixture reference pattern 302, similar to reference pattern 212, that is applied to or formed on a surface of the oral fixture 12. Also, in this embodiment, the tool 102 does not include a tool fixture 100 but, instead, includes a tool reference pattern 304, again similar to reference pattern 212. There are two cameras 306 mounted on the reference plate 200, one positioned so as to visually detect the location of the fixture reference pattern 302 and the other to visually detect the tool reference pattern 304. From the video data of those two patterns, the system is capable of correlating the CT scan to the actual orientation of the mouth and depict the location of the tool on the scan. Alternatively, instead of two cameras, the reference plate could have a single camera that has a wide enough field of view to visually detect each reference pattern on the tool and oral fixture.

Figure 14:
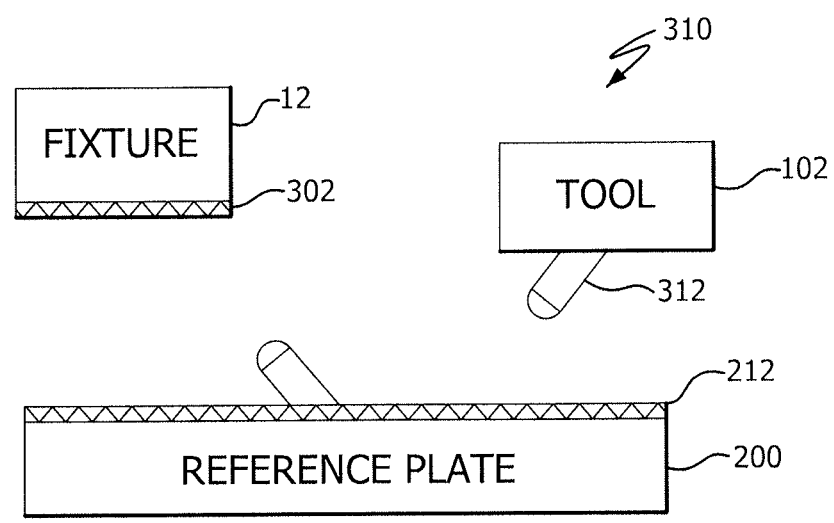
FIG. 14 is a schematic representation of another alternate embodiment of the present invention using an oral fixture, a reference fixture and a tool with a different arrangement of cameras and reference patterns.

Referring to FIG. 14, another embodiment 310 of the invention is shown. In this embodiment, the oral fixture 12 includes a fixture reference pattern 302 as discussed above. The tool 102 includes a tool fixture 100 similar to the tool fixture described above but with only one camera 312 oriented toward the reference pattern 212 on the reference plate 200. The reference plate 200 also includes a camera 306 mounted so as to detect the fixture reference pattern 302 on the oral fixture 12. From the video data from the two cameras and the detection of the two patterns, the system is capable of correlating the CT scan to the actual orientation of the mouth and depict the location of the tool on the scan.

Figure 15:
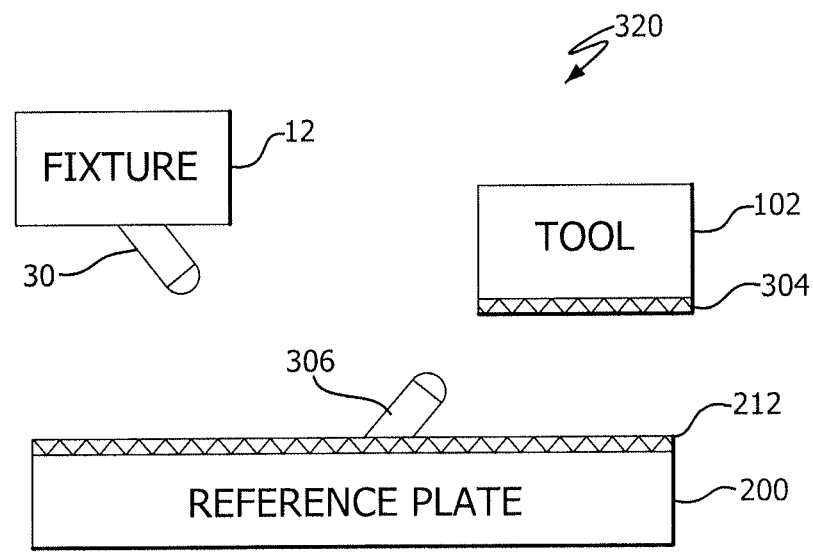
FIG. 15 is a schematic representation of another alternate embodiment of the present invention using an oral fixture, a reference fixture and a tool with a different arrangement of cameras and reference patterns.

Referring to FIG. 15, another embodiment 320 of the invention is shown. In this embodiment, the oral fixture 12 is similar to the one described with reference to FIG. 1 and includes a camera mount 26 and camera 30. In this embodiment, the tool 102 does not require a tool fixture 100 but, instead, includes a tool reference pattern 304 as discussed above with respect to FIG. 13. The reference plate 200 also includes a camera 306 mounted so as to detect the tool reference pattern 304 on the tool 102. The camera on oral fixture 12 is oriented to detect the reference pattern 212 on the reference plate 200. Using the video data from the two cameras and the detection of the two patterns, the system is capable of correlating the CT scan to the actual orientation of the mouth and depict the location of the tool on the scan.

Figure 16:
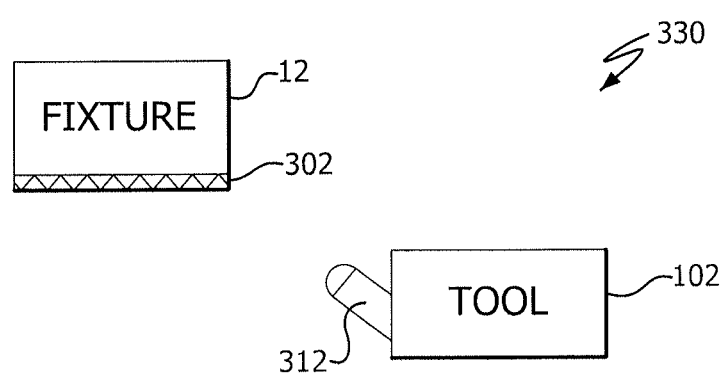
FIG. 16 is a schematic representation of an alternate embodiment of the present invention using an oral fixture and a tool with a different arrangement of cameras and/or reference patterns.

Referring to FIG. 16, a further variation of the invention 330 in shown. In this one, there is no reference plate 200 used. Instead, the oral fixture 12 includes a fixture reference pattern 302 as discussed above. The tool 102 includes a tool fixture similar to the tool fixture described above but with only one camera 312 oriented toward the fixture reference pattern 302 on the oral fixture 12. Using the video data from the camera on the tool 102 and the pattern on the oral fixture, the system is capable of correlating the CT scan to the actual orientation of the mouth and depict the location of the tool on the scan.

Figure 17:
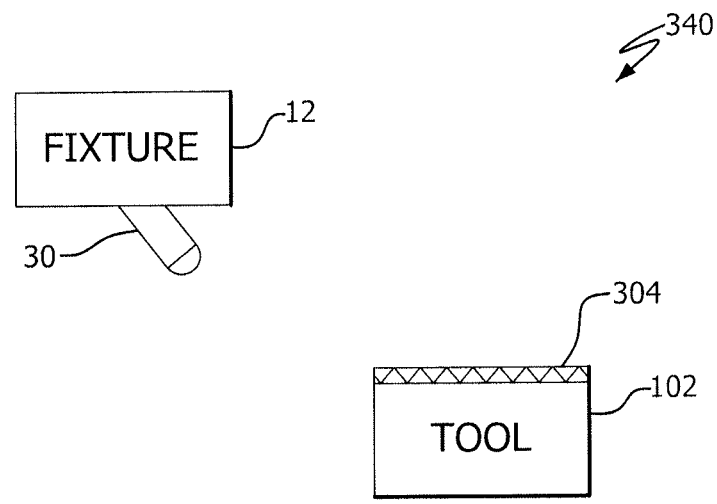
FIG. 17 is a schematic representation of another alternate embodiment of the present invention using an oral fixture and a tool with a different arrangement of cameras and/or reference patterns.

Referring to FIG. 17, a further embodiment 340 of the invention in shown. In this embodiment, there again is no reference plate 200 used. Instead, the oral fixture 12 includes a camera mount similar to the camera mount described with the camera 30 oriented toward the tool 102. The tool 102 includes a tool reference pattern 304 similar to the tool reference pattern described above with reference to FIG. 13. Using the video data from the camera on the oral fixture 12 and the pattern on the tool 102, the system is capable of correlating the CT scan to the actual orientation of the mouth and depict the location of the tool on the scan.

Figure 18:
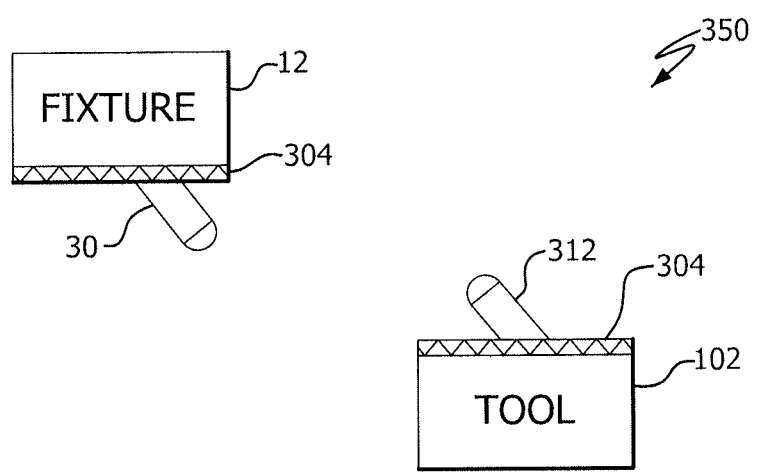
FIG. 18 is a schematic representation of another alternate embodiment of the present invention using an oral fixture and a tool with a different arrangement of cameras and/or reference patterns.

Referring to FIG. 18, another embodiment 350 of the invention in shown. In this embodiment, there again is no reference plate 200 used. Instead, the oral fixture 12 includes a camera mount similar to the embodiment in FIG. 17 oriented toward the tool 102. The tool 102 includes a camera 312 similar to the camera in FIG. 16. Both the tool and the fixture would include a reference pattern. The system uses the video data from the cameras to correlate the CT scan to the actual orientation of the mouth and depict the location of the tool on the scan.

In another variation of the invention, it is contemplated that a surgeon can use a camera, such as the cameras mounted to the tool fixture 100, to map the oral cavity of the patient on the day of surgery. In this embodiment, the oral fixture 12 and reference plate 200 would be formed and attached to the patient on the day of surgery. The surgeon can then create a 3D optical map of the patient's mouth using the tool cameras. Then, using the data from the 3D model and the prior CT scan, the system would reference the two together. In this embodiment, the oral fixture 12 does not need to be made in advance.

Figure 19:
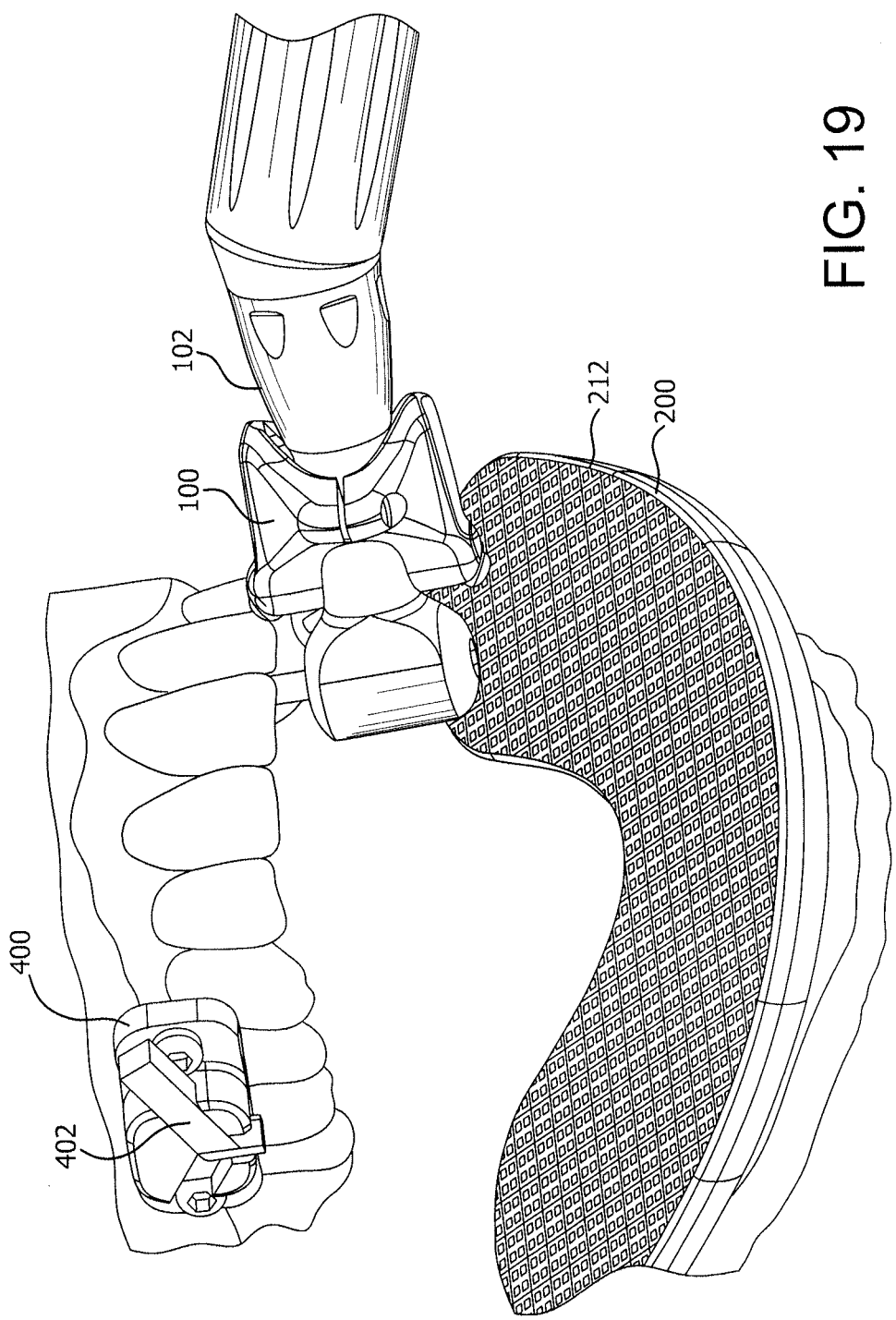
FIG. 19 is a representation of an oral fixture, reference fixture and tool fixture in use in a patient's mouth according to another embodiment of the invention where the oral fixture is fixedly attached to the patient's mouth.

The foregoing embodiments are based on the assumption that the patient has sufficient teeth to mount the oral fixture 12 and reference plate 200. If, however, the condition of the patient's mouth prevents attachment of either or both of the oral fixture 12 and reference plate 200, the present invention envisions that either component can be directly mounted to the jaw bone of the patient. This is depicted in FIG. 19, the oral fixture 400 is fixedly attached to the patient's upper jaw bone. The oral fixture includes a camera 402 oriented to detect the pattern 212 on the reference plate 200 as discussed above.

Also, it is contemplated that the fiducial markers 34 on the oral fixture 12 can be eliminated from the present invention. Instead, a scan of the patient can be used to detect the teeth as the fiducial markers, and the position of the camera relative to the teeth can be determined by the system.

It is also contemplated that the present invention can be conducted without use of any fiducials (fiducial-free). For example, a fixture containing a camera but no fiducials is attached to the patient at the time of surgery and the tool with an upward camera and a downward camera is passed over the teeth. As the tool is moved, the upward camera references itself with respect to the reference plate, as does the oral fixture's camera. This determines the relative position between the teeth to which the oral fixture is attached and the moving tool, allowing precise estimation of the tool's motion. This known motion, in turn, allows the downward camera to build a 3D model simultaneously estimating the structure and appearance of the teeth and gums. In this embodiment, only the 3D structure is used to register the optically-derived surfaces to the prior CT-derived surfaces that are produced, e.g., by marching cubes, thus providing the link between the oral fixture's camera and the CT coordinate system.

One of the benefits of the present invention is the elimination of the need for making cast models. Thus, the system and the fixture disclosed above expedite the overall surgical procedure and reduce the amount of patient discomfort.

In addition to movement of the patient, the program also is configured to receive optical data for determining the relative position of the surgical tools that are being used. Specifically, as discussed above, the tool fixture preferably includes a second camera 109 which provides an image of the tool bit 106 being used in the procedure. The system is designed to determine the location of the tool bit 106 in three dimensions and to adjust the position of a simulated surgical tool that is depicted on the display of the imaged data. Thus, the movement of the actual tool is mimicked by the simulated tool on the display.

In order to do so, at the start of the procedure, the doctor or technician must register the surgical instrument by entering the particular instrument into the software system, at which point the system retrieves the details on the instrument, including its tip, and may retrieve other features, such as length, shape, etc. Alternatively, and more preferably and with reference to FIG. 20, the doctor or technician uses a registration device 500 for providing optical data that can be used to determine the location of the tool bit 106 relative to the cameras 105, 109, as well as the length and diameter of the tool bit. The registration device 500 preferably includes a spherical touch pad 502 mounted to a base 504. A registration pattern 506 is formed on the registration device 500 at a defined location. In the illustrated embodiment, the pattern 506 is on the base 504, as well as wall 508 extending upward from the base 504. The pattern 506 is preferably similar to the non-repetitive pattern 212 referred to above.

In use, the doctor or technician inserts or touches the tip of the tool bit 106 on the touch pad 502. The registration program in the system is activated causing the cameras 105, 109 to receive video (optical) data. The registration pattern 506 is located so that one or both of the cameras 105, 109 can detect the pattern. Once the cameras are receiving data, the doctor or technician moves (rotates and pivots) the tool about its tip so that the camera(s) can capture the changes in the registration pattern 506. From the received data, the system can determine the location of the tip of the tool bit 106 relative to the cameras 105, 109. Repeating this procedure with two tool bits 106 with different lengths allows the system to determine the axis of the tool bit 106 with respect to each camera.

As noted above, one of the problems that can occur during an operation is that the surgeon may change the surgical instrument or the tip of the instrument, thus potentially interfering with the accuracy of the imaged depiction of the surgical tool unless the new tip or new surgical tool is reregistered. Sometimes, the complexities of the surgical procedure make reregistering the tool difficult or result in the surgeon inadvertently forgetting to register the tool. The present invention addresses that issue by setting a surgical zone or boundary that is based on continuous detection of the reference pattern 212. More specifically, once a surgical procedure has commenced and the system detects the reference pattern 212 on the reference plate 200 (or the fixture pattern 302), the tool 102 is considered to be with the boundary volume of the oral cavity.

Since the program can track the tool 102 by monitoring the reference pattern 212 (or fixture pattern 302), it can be used to determine if the doctor potentially has made a change to the surgical instrument. For example, the program detects when the cameras on the tool 102 first see the reference pattern (or fixture pattern) after initial registration of the tool. It then continues to monitor the tool 102 after registration. If the cameras continue to detect the reference pattern (or fixture pattern), the program presumes that no changes have been made to the tool 102. However, if the cameras on the tool 102 do not detect the reference pattern (or fixture pattern) for a prescribed period of time, the program determines that the tool 102 has likely left the oral cavity and requires the doctor to take an additional step before continuing with the procedure. In one embodiment, the program sends a pop-up message to the display informing the doctor that they have moved out of the oral cavity and requiring them to either confirm that no change has been made to the surgical tool 102 or to register the new tool on the registration device 500. Once the doctor responds, the pop-up display disappears and the doctor can continue to see the full display.

Thus, the present invention provides a novel method for tracking the surgical tool being used in an image guided surgical procedure and notifying the doctor to confirm whether tool changes have been made.

While the above description refers to a surgical tool or instrument that includes a drill, the term "surgical instrument" or "surgical tool" is intended to cover other tools used during intraoral procedures, such as ablation tools for ablating tissue, including third molars in children.

The system or systems described herein may be implemented on any form of computer or computers and the components may be implemented as dedicated applications or in client-server architectures, including a web-based architecture, and can include functional programs, codes, and code segments. The system of the present invention may include a software program be stored on a computer and/or storage device (e.g., mediums), and/or may be executed through a network. The method may be implemented through program code or program modules stored on a storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The embodiments herein may be described in terms of various processing steps. Such processing steps may be realized by any number of hardware and/or software components that perform the specified functions. For example, the described embodiments may employ various integrated circuit components, e.g., memory elements, processing elements, logic elements, look-up tables, and the like, which may carry out a variety of functions under the control of one or more microprocessors or other control devices. Similarly, where the elements of the described embodiments are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the embodiments of the invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the steps of all methods described herein are performable in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

The invention claimed is:

1. An oral fixture for an image guidance system for tracking and depicting movement of a surgical tool during oral surgery, the oral fixture removably attachable to at least one tooth in a patient's mouth, the oral fixture comprising:
a plastic support made from a rigid material that will not substantially deform when subjected to temperatures of about 100 degrees F., the support including a base with an inner wall and an outer wall, the inner wall and outer wall extending outward at an angle from the base, the inner and outer walls being spaced from each other so as to be adapted to receive a tooth to which the oral fixture is intended to be attached;
a moldable thermoplastic material located on an inner surface of the support, the moldable material configured upon curing to retain an impression of the outside contours of a portion of a patient's teeth that were covered by the material;
a mount on an outside surface of the outer wall for holding a tracking component in an image guidance system; and
at least three fiducial markers rigidly attached to an outer surface of the base for use in determining the location of the oral fixture relative to the patient's teeth, the fiducial markers being made from a material that has a different radiodensity than the support, the moldable material and the patient's teeth so as to be detectable in a CT scan, the fiducial markers being spaced apart from one another in a triangular pattern with at least two fiducial markers located substantially in line with one of either the inner or outer walls, and the other fiducial marker located substantially in line with the other of either the inner or outer walls.

2. An oral fixture for an image guidance system according to claim 1, wherein at least one of the base, inner wall and outer wall of the oral fixture support includes surface irregularities which assist in securing or attaching the moldable material.

3. An oral fixture for an image guidance system according to claim 1, wherein the moldable material of the oral fixture is configured to become initially moldable when placed in a liquid bath at an elevated temperature above a mold temperature.

4. An oral fixture for an image guidance system according to claim 3, wherein the moldable material of the oral fixture is configured to provide a visual indication when the material is ready to be molded.

5. An oral fixture for an image guidance system according to claim 4, wherein the visual indication is a change in color of at least a portion of the moldable material.

6. An oral fixture for an image guidance system according to claim 3, wherein the moldable material of the oral fixture is preferably a polycaprolactone or a polyvinylsiloxane (PVS) material.

7. An oral fixture for an image guidance system according to claim 1, wherein the support and the moldable material of the oral fixture are sized to cover at least two adjacent teeth of a patient.

8. An oral fixture for an image guidance system according to claim 1, wherein the support of the oral fixture includes lines of weakening at different points along a length of the support which permit the support to be broken to a desired length for sizing to a particular patient's mouth.

9. An oral fixture for an image guidance system according to claim 1, wherein the mount includes at least one camera mount that is attached to or formed integral with the support, the camera mount including at least one camera holder into which a camera may be mounted for viewing a surface in front of or on the opposite side of the mouth from the fixture.

10. An oral fixture for an image guidance system according to claim 9, wherein the camera holder of the oral fixture is a channel or hole formed in the camera mount that is sized to receive a small video camera.

11. An oral fixture for an image guidance system according to claim 10, wherein there are two channels in the camera mount of the oral fixture that are positioned to orient two cameras in two different directions relative to the support, each channel oriented at an angle between about 5 and about 45 degrees on either side of a vertical access.

12. An oral fixture for an image guidance system according to claim 1, further comprising a tracking component attached to the mount, the tracking component includes an optical pattern, and wherein the mount attaches the optical pattern to the support.

13. An oral fixture for an image guidance system according to claim 1, wherein each fiducial marker has a radiodensity, size or shape that is different than the other fiducial markers so as to be automatically detectable by a tracking software.

14. An oral fixture for an image guidance system according to claim 1, wherein the fiducial markers are ceramic ball bearings.

15. An oral fixture for an image guidance system according to claim 1, wherein the fiducial markers are each mounted in a hole formed through the base and into the inner or outer walls.

16. An oral fixture for an image guidance system according to claim 15, wherein there are a plurality of slotted cut-outs in the support, each slotted cut-out extending through a portion of the base and either the inner wall or the outer wall.

17. An oral fixture for an image guidance system according to claim 1, wherein there are a plurality of slotted cutouts in the support, each slotted cut-out extending through a portion of the base and either the inner wall or the outer wall.

18. An image guidance system for tracking and depicting movement of an oral surgical tool during oral surgery, the system comprising:
- an oral fixture according to claim 1;
- a tool fixture mounted to or part of a dental surgical tool;
- a reference fixture mountable to a patient's teeth separate from the oral fixture, the reference fixture including a reference pattern on a surface of the reference fixture, the reference pattern configured to provide visual reference points for a video camera to detect for use in determining the position of the oral fixture; and
- tracking software configured to track movement of the tool fixture relative to the oral fixture and to depict the relative motion on a stored image of a patient's mouth.

* * * * *